US011116795B2

(12) United States Patent
Mason et al.

(10) Patent No.: US 11,116,795 B2
(45) Date of Patent: Sep. 14, 2021

(54) TREATMENT OF A CANINE CD20 POSITIVE DISEASE OR CONDITION USING A CANINE CD20-SPECIFIC CHIMERIC ANTIGEN RECEPTOR

(71) Applicant: THE TRUSTEES OF THE UNIVERSITY OF PENNSYLVANIA, Philadelphia, PA (US)

(72) Inventors: Nicola Mason, Philadelphia, PA (US); Daniel J. Powell, Jr., Bala Cynwyd, PA (US); Mohammed Kazim Panjwani, Philadelphia, PA (US); Jenessa Smith, San Diego, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 390 days.

(21) Appl. No.: 15/743,033

(22) PCT Filed: Jul. 8, 2016

(86) PCT No.: PCT/US2016/041557
§ 371 (c)(1),
(2) Date: Jan. 9, 2018

(87) PCT Pub. No.: WO2017/011316
PCT Pub. Date: Jan. 19, 2017

(65) Prior Publication Data
US 2019/0350972 A1 Nov. 21, 2019

Related U.S. Application Data

(60) Provisional application No. 62/191,048, filed on Jul. 10, 2015.

(51) Int. Cl.
| *A61K 35/17* | (2015.01) |
| *A61P 35/00* | (2006.01) |
| *C12N 5/0783* | (2010.01) |
| *C07K 14/725* | (2006.01) |
| *C07K 14/705* | (2006.01) |
| *C07K 16/28* | (2006.01) |
| *A61K 39/00* | (2006.01) |

(52) U.S. Cl.
CPC ...... *A61K 35/17* (2013.01); *A61K 39/001124* (2018.08); *A61P 35/00* (2018.01); *C07K 14/7051* (2013.01); *C07K 14/70517* (2013.01); *C07K 14/70521* (2013.01); *C07K 14/70578* (2013.01); *C07K 16/2887* (2013.01); *C12N 5/0638* (2013.01); *A61K 2039/552* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| 7,261,890 B2 | 8/2007 | Krah et al. | |
| 2011/0091483 A1 | 4/2011 | Beall et al. | |
| 2013/0287748 A1* | 10/2013 | June | C07K 14/70521 424/93.21 |
| 2014/0322212 A1 | 10/2014 | Brogdon et al. | |
| 2014/0370045 A1 | 12/2014 | June et al. | |
| 2017/0183407 A1* | 6/2017 | Cooper | A61P 31/04 |

FOREIGN PATENT DOCUMENTS

WO 03060080 A2 7/2003

OTHER PUBLICATIONS

O'Connor et al., (2013). Chimeric antigen receptor T-cell therapy for companion canines with spontaneous B-cell non-Hodgkin lymphoma. Mol Ther 21: S249. (Year: 2013).*
Jubala et al. CD20 Expression in Normal Canine B Cells and in Canine non-Hodgkin Lymphoma. Vet Pathol 42:468-476 (2005) (Year: 2005).*
Rudikoff et al., Single amino acid substitution altering antigen-binding specificity. Proc. NatL Acad. Sci. USA vol. 79, pp. 1979-1983, Mar. 1982 (Year: 1982).*
Winkler et al. Changing the Antigen Binding Specificity by Single Point Mutations of an Anti-p24 (HIV-1) Antibody. Journal of Immunology, 2000, 165: 4505-4514. (Year: 2000).*
Dechant et al., Direct submission, Oct. 9, 2001, anti-human CD20 antibody 1F5 gamma heavy chain variable region [Mus musculus] Gen Bank: AAL27650.1 (Year: 2001).*
Dechant et al., Direct submission, Oct. 9, 2001, anti-human CD20 antibody 1F5 kappa light chain variable region [Mus musculus] Gen Bank: AAL27649.1 (Year: 2001).*
Press et al., Monoclonal Antibody 1 F5 (Anti-CD20) Serotherapy of Human B Cell Lymphomas. Blood, vol. 69, No. 2 (Feb. 1987): pp. 584-591 (Year: 1987).*
International Search Report dated Dec. 1, 2016 in International Application No. PCT/US16/41557.
Mata , et al., "Towards immunotherapy with redirected T cells in a large animal model: Ex vivo activation, expansion, and genetic medication of canine T cells", J. Immunother, 37(8), Oct. 2014, 407-415.
Sasai , et al., "Monoclonal Antibodies for the Diagnosis of Canine Mastocytoma", Hybridoma, vol. 26(3), Jun. 2007, Abstract only.
Smith , et al., "Feasibility and safety of cCD20 RNA CAR-bearing T cell therapy for the treatment of canine B cell malignancies", J. Immunotherapy of Cancer, 3(Suppl.2), Nov. 2015, 123.
Aguiar , et al., "Production of Monoclonal Antibodies Against Canine Leukocytes", Hybridoma and Hybridomics 23(2), 2004, 127-132.

* cited by examiner

*Primary Examiner* — Arthur S Leonard
(74) *Attorney, Agent, or Firm* — Saul Ewing Arnstein & Lehr LLP; Kathryn Doyle

(57) ABSTRACT

The present invention relates to compositions and methods for the treatment of a canine CD20 positive disease or condition using a canine CD20-specific chimeric antigen receptor. One aspect includes a modified canine T cells and pharmaceutical compositions comprising the modified cells for adoptive cell therapy and treating a disease or condition associated with enhanced immunity in canine.

38 Claims, 13 Drawing Sheets

Specification includes a Sequence Listing.

Day 3

A

B

A

B

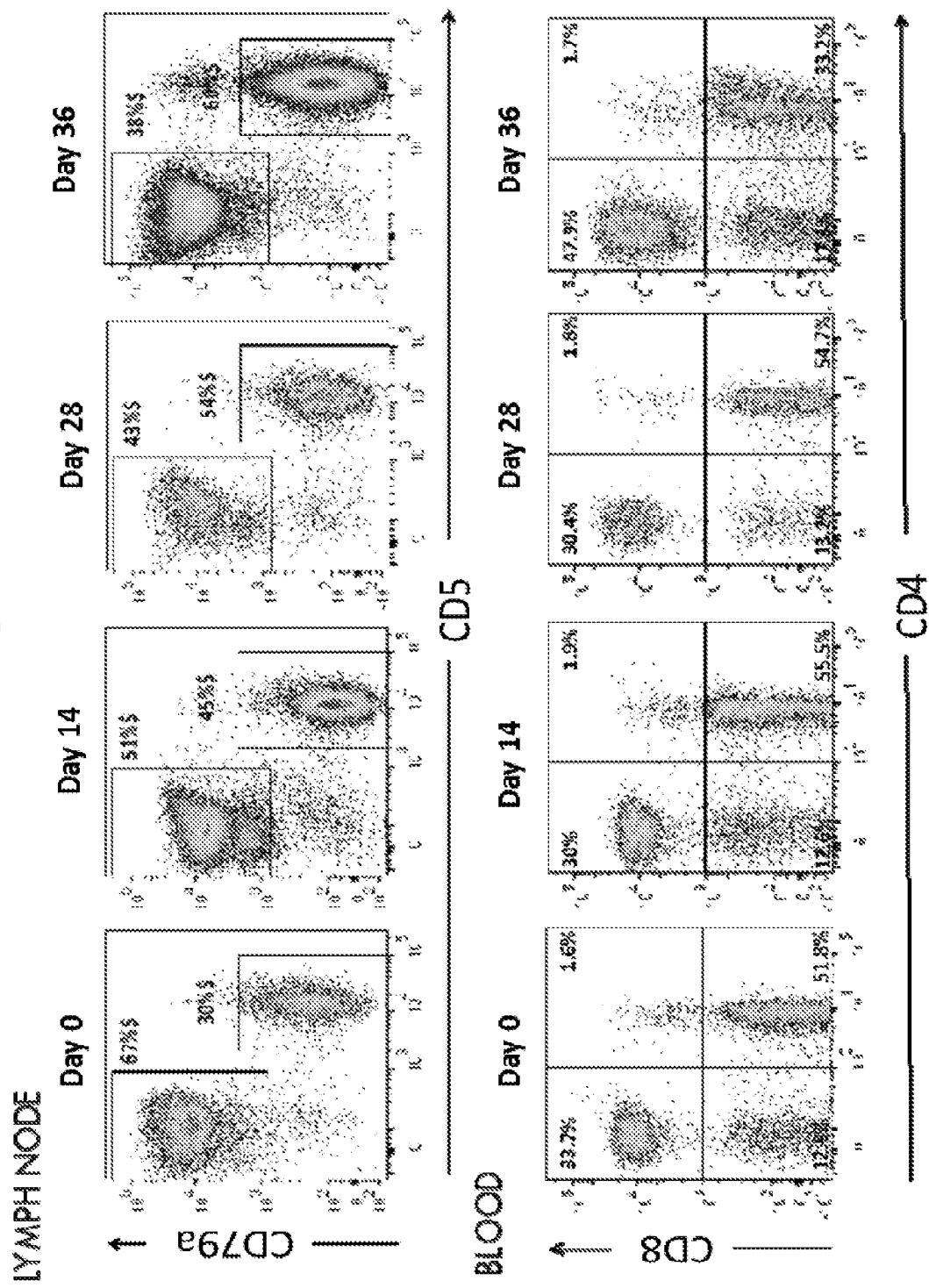

TREATMENT OF A CANINE CD20 POSITIVE DISEASE OR CONDITION USING A CANINE CD20-SPECIFIC CHIMERIC ANTIGEN RECEPTOR

CROSS REFERENCE TO RELATED APPLICATIONS

This application is a 35 U.S.C. § 371 national phase application from, and claims priority to, International Application No. PCT/US2016/041557, filed Jul. 8, 2016 and published under PCT Article 21(2) in English, which claims priority under 35 U.S.C. § 119(e) to U.S. Provisional Patent Application No. 62/191,048, filed Jul. 10, 2015, which are hereby incorporated by reference in their entirety herein.

BACKGROUND OF THE INVENTION

Cancer immunotherapy has demonstrated exciting clinical results in the setting of numerous solid tumors and hematologic malignancies. The endogenous immune system is typically non-reactive to malignant cells, or even actively immunosuppressive. One way to circumvent this phenomenon is by forcing tumor recognition by genetic engineering of lymphocytes. T cells can be engineered to express a synthetic immunoreceptor comprised of an extracellular targeting single chain variable fragment (scFv) linked to an intracellular signaling domain, known as a chimeric antigen receptor (CAR). Genetically modified T cells can be expanded ex vivo and then transferred back into the donor patient. This new area of research is referred to as adoptive CAR T cell therapy. In humans, T cell therapy has been used against many different tumor histologies, including lymphoma, melanoma, and colon cancer.

Cancer is the leading cause of death for domestic dogs. Domestic dogs are unique from other animal models of cancer in that they spontaneously develop tumors that have similar biologic and genetic features to human spontanoues tumors. (e.g. B cell Non-Hodgkin's Lymphoma, Malignant Melanoma and Osteosarcoma). B cell lymphoma affects $30/100,000$ dogs per year. Standard of care treatment for dogs with spontaneous B cell NHL is based on chemotherapy and it provides a median survival time of about 1 year. Current treatment induces remission in about 75 percent of dog-patients but the majority of them relapse with drug resistant disease shortly thereafter. Many rescue protocols have been described that offer the hope of a second or third remission, however, these remissions, if attained, are usually of short duration and dogs eventually succumb to their disease. There is a significant demand for improved therapies for dogs with this common cancer. CAR T cells offer the possibility of long-term remission/cure of this disease. However, in canines this approach is still at a primitive stage and has currently only been tested ex vivo in a few different types of tumors.

There is a great need in the art for more effective methods to combat cancer in dogs. This invention addresses this need.

SUMMARY OF THE INVENTION

In one aspect, the invention includes an isolated nucleic acid sequence encoding a chimeric antigen receptor (CAR) comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

In another aspect, the invention includes a vector comprising an isolated nucleic acid sequence encoding a CAR comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

Yet another aspect of the invention includes an isolated CAR comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

Another aspect of the invention includes a cell comprising (a) an isolated nucleic acid sequence encoding a CAR, or (b) an isolated CAR, comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

Yet another aspect of the invention includes a modified cell comprising a nucleic acid sequence encoding a CAR comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

In another aspect, the invention includes a composition comprising a modified cell comprising (a) an isolated nucleic acid sequence encoding a CAR, or (b) an isolated CAR, comprising a canine CD20 antigen binding domain, a transmembrane domain, a costimulatory signaling region, and a CD3 zeta signaling domain, wherein the canine CD20 antigen binding domain comprises a CD20 antibody or a fragment thereof.

Another aspect of the present invention includes use of a modified cell comprising a nucleic acid sequence encoding a CAR comprising a canine CD20 antigen binding domain, a transmembrane domain, a costimulatory signaling region, and a CD3 zeta signaling domain, wherein the canine CD20 antigen binding domain comprises a CD20 antibody or a fragment thereof, in the manufacture of a medicament for the treatment of cancer in a subject in need thereof.

Yet another aspect of the present invention includes a pharmaceutical composition comprising a modified cell comprising a nucleic acid sequence encoding a CAR comprising a canine CD20 antigen binding domain, a transmembrane domain, a costimulatory signaling region, and a CD3 zeta signaling domain, wherein the canine CD20 antigen binding domain comprises a CD20 antibody or a fragment thereof and a pharmaceutically acceptable carrier.

Still another aspect of the present invention includes a method for stimulating a T cell-mediated immune response in a canine. The method of the invention comprises administering to the canine an effective amount of a modified cell that expresses a CAR comprising a canine CD20 antigen binding domain, a transmembrane domain, a costimulatory signaling region, and a CD3 zeta signaling domain, wherein the canine CD20 antigen binding domain comprises an CD20 antibody or a fragment thereof.

Another aspect of the invention includes a method of treating a canine with disease or condition. The method of the invention comprises administering to the canine a modified canine T cell that expresses a CAR comprising a canine CD20 antigen binding domain, a transmembrane domain, a costimulatory signaling region, and a CD3 zeta signaling domain, wherein the canine CD20 antigen binding domain comprises an CD20 antibody or a fragment thereof and wherein the disease or condition is a cancer and/or an autoimmune disease.

In one embodiment, the CAR comprises a sequence selected from the group consisting of SEQ ID NOs: 3-6. In another embodiment, the CAR is encoded by a sequence selected from the group consisting of SEQ ID NOs: 3-6.

In another embodiment, the canine CD20 antigen binding domain comprises a heavy and light chain. In yet another embodiment, the canine CD20 antigen binding domain is an antibody selected from the group consisting of a canine antibody, a caninized antibody, and a fragment thereof. In still another embodiment, the canine CD20 antigen binding domain is selected from the group consisting of a Fab fragment, a F(ab')$_2$ fragment, a Fv fragment, and a single chain Fv (scFv).

In another embodiment, the canine CD20 antigen binding domain specifically binds to CD20 expressed by tumor cells and/or tumor vasculature. In yet another embodiment, the tumor cells are from a cancer selected from the group consisting of lymphoma, Hodgkin lymphoma, non-Hodgkin lymphoma, lymph nodes cancer, bone marrow cancer, liver cancer, spleen cancer, ovarian cancer, renal cell carcinoma, bladder cancer, kidney cancer, testicular cancer, prostate cancer, breast cancer, colon cancer, pancreatic cancer, lung cancer, stomach cancer, eye cancer, skin cancer and any combination thereof.

In yet another embodiment, the costimulatory signaling region comprises an intracellular domain of a costimulatory molecule selected from the group consisting of CD8, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof. In another embodiment, the nucleic acid sequence is selected from the group consisting of a DNA and an mRNA.

In another embodiment, the modified cell is selected from the group consisting of a T cell, a natural killer (NK) cell, a cytotoxic T lymphocyte (CTL), and a regulatory T cell. In yet another embodiment, the nucleic acid sequence is introduced into the cell by at least one procedure selected from the group consisting of electroporation, usage of a lentivirus, usage of a retrovirus and a chemical-based transfection.

In another embodiment, the modified canine T cell is autologous to the subject. Yet another embodiment includes further administering an antitumor vaccine to the canine. In yet another embodiment, the modified canine T cell and the antitumor vaccine are co-administered to the canine.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments, which are presently preferred. It should be understood, however, that the invention is not limited to the precise arrangements and instrumentalities of the embodiments shown in the drawings.

FIG. 6B: IFNγ is secreted by CD20-z RNA CAR canine PBMCs in response to CD20$^{+(high)}$, but less so in CD20$^{+/-(high)}$ tumor or engineered cells.

FIG. 7A highlights the difference between canine PBCMs untransduced and transduced with lentivirus containing canine CD20-CAR. FIG. 7B shows expansion of the antigen specific CAR+ T cell following 2 rounds of co-culture with the canine CD20+ B cell lymphoma cell line, CLBL-1.

FIG. 9 is a series of flow cytometric plots depicting cell types present in a single target lymph node evaluated at the time points indicated (upper panel) and changes in the percentages of CD4+ and CD8+ T cells in the peripheral blood following CART cell infusion (lower panel).

DETAILED DESCRIPTION

Definitions

Figure 1A:
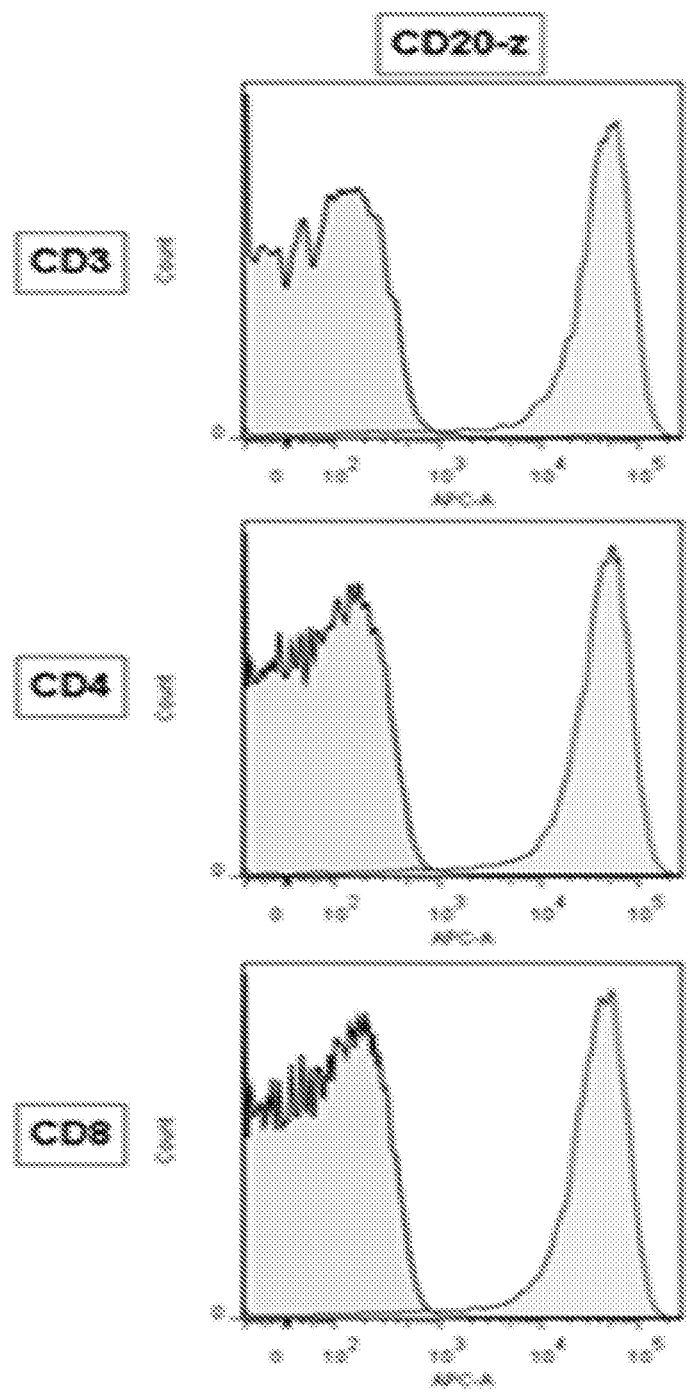
FIGS. 1A-1C are a series of graphs and histograms demonstrating very high expression of the CD20-z CAR RNA in nearly 100% of canine CD3$^+$, CD4$^+$ and CD8$^+$ PBMC populations 24 hours post electroporation (10 ug of RNA).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and caninized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "arming" as used herein refers to displaying the bispecific antibody on the surface of the cell. In one embodiment, the bispecific antibody specifically binds to an antigenic epitope on the cell to be armed with the bispecific antibody, such as a T cell, and binds another antigenic epitope, such as an antigenic epitope on a target cell, such as another cell.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, spleen cancer, colorectal cancer, renal cancer, liver cancer, brain cancer, lymphoma, leukemia, Hodgkin lymphoma, non-Hodgkin lymphoma, lymph nodes cancer, bone marrow cancer, lung cancer, stomach cancer, eye cancer and the like.

"Caninized" forms of non-canine (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-canine immunoglobulin. For the most part, caninized antibodies are canine immunoglobulins (recipient antibody) in which residues from a complementary-determining region (CDR) of the recipient are replaced by residues from a CDR of a non-canine species (donor antibody) such as mouse, rat or rabbit having the desired specificity, affinity, and capacity. In some instances, Fv framework region (FR) residues of the canine immunoglobulin are replaced by corresponding non-canine residues. Furthermore, caninized antibodies can comprise residues which are found neither in the recipient antibody nor in the imported CDR or framework sequences. These modifications are made to further refine and optimize antibody performance. In general, the caninized antibody will comprise substantially all of at least one, and typically two, variable domains, in which all or substantially all of the CDR regions correspond to those of a non-canine immunoglobulin and all or substantially all of the FR regions are those of a canine immunoglobulin sequence. The caninized antibody optimally also will comprise at least a portion of an immunoglobulin constant region (Fc), typically that of a canine immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully canine" refers to an immunoglobulin, such as an antibody, where the whole molecule is of canine origin or consists of an amino acid sequence identical to a canine form of the antibody.

The term "chimeric antigen receptor" or "CAR." as used herein, refers to an artificial cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs have been expressed with specificity for a tumor associated antigen, for example. CARs may also comprise an intracellular activation domain, a transmembrane domain and an extracellular domain comprising a tumor associated antigen binding region. In some aspects, CARs comprise fusions of single-chain variable fragments (scFv) derived monoclonal antibodies, fused to CD3-zeta transmembrane and intracellular domain. The specificity of CAR designs may be derived from ligands of receptors (e.g., peptides). In some embodiments, a CAR can target cancers by redirecting the specificity of a T cell expressing the CAR specific for tumor associated antigens.

The term "chimeric intracellular signaling molecule" refers to recombinant receptor comprising one or more intracellular domains of one or more co-stimulatory molecules. The chimeric intracellular signaling molecule substantially lacks an extracellular domain. In some embodiments, the chimeric intracellular signaling molecule comprises additional domains, such as a transmembrane domain, a detectable tag, and a spacer domain.

The term "codon optimization" as used herein is intended to refer to technique aimed to improve and maximize the protein expression in living organism by increasing the translational efficiency of gene of interest by transforming/replacing DNA sequence of nucleotides of one species into DNA sequence of nucleotides of another species. Codon optimization involves replacing wild type DNA sequences and rare codons by more highly expressed species sequences and frequently occurring codons without changing the protein.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD8, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD8, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

A "co-stimulatory signal", as used herein, refers to a signal, which in combination with a primary signal, such as TCR/CD3 ligation, leads to T cell proliferation and/or upregulation or downregulation of key molecules.

The term "cytotoxic" or "cytotoxicity" refers to killing or damaging cells. In one embodiment, cytotoxicity of the modified cells is improved, e.g. increased cytolytic activity of T cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a dog) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. As applied to the nucleic acid or protein, "homologous" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

The guide nucleic acid sequence may be complementary to one strand (nucleotide sequence) of a double stranded DNA target site. The percentage of complementation between the guide nucleic acid sequence and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The guide nucleic acid sequence can be at least 10, 11, 12, 13, 14, 15, 16, 17, 18, 19, 20, 21, 22, 23, 24, 25, 26, 27, 28, 29, 30, 31, 32, 33, 34, 35 or more nucleotides in length. In some embodiments, the guide nucleic acid sequence comprises a contiguous stretch of 10 to 40 nucleotides. The variable targeting domain can be composed of a DNA sequence, a RNA sequence, a modified DNA sequence, a modified RNA sequence (see for example modifications described herein), or any combination thereof.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a canine.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "resistance to immunosuppression" refers to lack of suppression or reduced suppression of an immune system activity or activation.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or another non-human mammal. Non-human mammals include, for example, livestock and pets, such as ovine, bovine, porcine, canine, feline and murine mammals. Preferably, the subject is a canine.

As used herein, the term "substantially lacks an extracellular domain" refers to a molecule that is essentially free of a domain that extrudes extracellularly. In one embodiment, the chimeric intracellular signaling molecule lacks any function performed by an extracellular domain, such as antigen binding. In another embodiment, the chimeric intracellular signaling molecule includes a transmembrane domain but lacks a functional extracellular domain.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing major histocompatibility complex molecules (MHC). TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The term "tumor" as used herein, refers to an abnormal growth of tissue that may be benign, pre-cancerous, malignant, or metastatic.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions and methods for the treatment of canine CD20 positive malignancies and/or B cells using a canine CD20-specific chimeric antigen receptor. According to the invention, canine T cells are modified for adoptive T cell therapy in canines by expressing a canine CD20-specific chimeric antigen receptor. The modified canine T cells of this invention have improved cytotoxicity and resistance to immunosuppression imposed by tumor microenvironments.

Chimeric Antigen Receptor (CAR)

In one aspect of the invention, a T cell is generated by expressing a CAR therein. Thus, the present invention encompasses a CAR and a nucleic acid construct encoding a CAR, wherein the CAR includes an antigen binding domain, a transmembrane domain and an intracellular domain.

In one aspect, the invention includes a modified cell comprising a chimeric antigen receptor (CAR), wherein the CAR comprises an antigen binding domain, a transmembrane domain and an intracellular domain of a co-stimulatory molecule, and wherein the cell is a T cell that possesses targeted effector activity. In another aspect, the invention includes a modified cell comprising a nucleic acid sequence encoding a chimeric antigen receptor (CAR), wherein nucleic acid sequence comprises a nucleic acid sequence encoding an antigen binding domain, a nucleic acid sequence encoding a transmembrane domain and a nucleic acid sequence encoding an intracellular domain of a co-stimulatory molecule, and wherein the cell is a T cell that expresses the CAR and possesses targeted effector activity (e.g. targeted cellular cytotoxicity and antigen presentation). In one embodiment, the targeted effector activity is directed against an antigen on a target cell that specifically binds the antigen binding domain of the CAR. In one aspect, the target antigen is canine CD20 and the CAR comprises a canine anti-CD20 antigen binding domain.

In one aspect, the antigen binding domain of a CAR of the invention (e.g., a scFv) is encoded by a nucleic acid molecule whose sequence has been codon optimized for expression in a mammalian cell. In another aspect, the entire CAR construct of the invention is encoded by a nucleic acid molecule whose entire sequence has been codon optimized for expression in a mammalian cell. In some embodiments, the isolated nucleic acid sequence encoding the CAR is codon optimized to favor an increase in gene expression, translation efficiency and/or protein expression. A variety of codon optimization methods is known in the art, and include, e.g., methods disclosed in at least U.S. Pat. Nos. 5,786,464 and 6,114,148.

Antigen Binding Domain

In one embodiment, the CAR of the invention comprises a canine anti-CD20 antigen binding domain that binds to canine CD20 on a target cell. Examples of other cell surface markers that may act as an antigen that binds to the antigen binding domain of the CAR include those associated with viral, bacterial and parasitic infections, autoimmune disease, and cancer cells.

The choice of antigen binding domain depends upon the type and number of antigens that are present on the surface of a target cell. For example, the antigen binding domain may be chosen to recognize an antigen that acts as a cell surface marker on a target cell associated with a particular disease state.

The antigen binding domain can include any domain that binds to the antigen and may include, but is not limited to, a monoclonal antibody, a polyclonal antibody, a synthetic antibody, a canine antibody, a canonized antibody, a non-canine antibody, a human antibody, a humanized antibody, a non-human antibody, and any fragment thereof. Thus, in one embodiment, the antigen binding domain portion comprises a mammalian antibody or a fragment thereof. In another embodiment, the antigen binding domain of the CAR is selected from the group consisting of an anti-CD20 antibody and a fragment thereof.

In some instances, it is beneficial for the antigen binding domain to be derived from the same species in which the CAR will ultimately be used in. For example, for use in canines, it may be beneficial for the antigen binding domain of the CAR to comprise a canine antibody, canonized antibody as described elsewhere herein, or a fragment thereof.

It is also beneficial that the antigen binding domain is operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9. In some instances, a variety of canine hinges can be employed as well including the canine Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise the cytoplasmic domain of the CAR includes a similar or the same intracellular domain as the chimeric intracellular signaling molecule described elsewhere herein, and is responsible for activation of the cell in which the CAR is expressed.

In one embodiment, the intracellular domain of the CAR includes a domain responsible for signal activation and/or transduction.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD8, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

In one embodiment, the intracellular domain of the CAR includes any portion of one or more co-stimulatory molecules, such as at least one signaling domain from CD3, CD8, CD27, CD28, ICOS, 4-1BB, PD-1, any derivative or variant thereof, any synthetic sequence thereof that has the same functional capability, and any combination thereof.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

Canine Antibodies

It may be preferable to use canine antibodies or fragments thereof when using the antigen binding domains of a CAR. Completely canine antibodies are particularly desirable for therapeutic treatment of canine subjects. Canine antibodies can be made by a variety of methods known in the art including phage display methods using antibody libraries derived from canine immunoglobulin sequences, including improvements to these techniques. See, also, U.S. application Ser. No. 12/941,583; U.S. Pat. No. 7,261,890; and PCT publication WO 03/060080; each of which is incorporated herein by reference in its entirety.

Canine antibodies can also be produced using transgenic mice which are incapable of expressing functional endogenous immunoglobulins, but which can express canine immunoglobulin genes. For example, the canine heavy and light chain immunoglobulin gene complexes may be introduced randomly or by homologous recombination into mouse embryonic stem cells. Alternatively, the canine variable region, constant region, and diversity region may be introduced into mouse embryonic stem cells in addition to the canine heavy and light chain genes. The mouse heavy and light chain immunoglobulin genes may be rendered non-functional separately or simultaneously with the introduction of canine immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express canine antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The canine immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing canine antibodies, see, Aguiar et al. (Hybrid Hybridomics., 23(2):127-32 (2004)). In addition, companies such as Creative Biolabs (Shirley, N.Y.) and AbD Serotec (Raleigh, N.C.) can be engaged to provide canine antibodies directed against a selected antigen using technology similar to that described above.

Canine antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce canine antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized canine donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Canine antibodies may also be generated by in vitro activated B cells. Canine antibodies may also be generated in vitro using hybridoma techniques such as, but not limited to, that described by Sasai et al. (Hybridoma., 26(3):162-7 (2007)).

"Caninized" Antibodies

Alternatively, in some embodiments, a non-canine antibody can be caninized, where specific sequences or regions of the antibody are modified to increase similarity to an antibody naturally produced in a canine. For instance, in the present invention, the antibody or fragment thereof may comprise a non-canine mammalian scFv. In one embodiment, the antigen binding domain portion is caninized.

A caninized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A caninized antibody has one or more amino acid residues introduced into it from a source which is non-canine. These non-canine amino acid residues are often referred to as "import" residues, which are typically taken from an "import" variable domain. Thus, caninized antibodies comprise one or more CDRs from non-canine immunoglobulin molecules and framework regions from canine. Caninization of antibodies is well-known in the art and can essentially be performed by substituting rodent CDRs or CDR sequences for the corresponding sequences of a canine antibody (U.S. patent application Ser. No. 10/327,598 the content of which is incorporated herein by reference herein in its entirety). In such caninized chimeric antibodies, substantially less than an intact canine variable domain has been substituted by the corresponding sequence from a non-canine species. In practice, caninized antibodies are typically canine antibodies in which some CDR residues and possibly some framework (FR) residues are substituted by residues from analogous sites in rodent antibodies. Caninization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of canine variable domains, both light and heavy, to be used in making the caninized antibodies is to reduce antigenicity. According to the so-called "best-fit" method, the sequence of the variable domain of a rodent antibody is screened against the entire library of known canine variable-domain sequences. The canine sequence which is closest to that of the rodent is then accepted as the canine framework (FR) for the caninized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all canine antibodies of a particular subgroup of light or heavy chains. The same framework may be used for several different caninized antibodies.

Antibodies can be caninized with retention of high affinity for the target antigen and other favorable biological properties. According to one aspect of the invention, caninized antibodies are prepared by a process of analysis of the parental sequences and various conceptual caninized products using three-dimensional models of the parental and caninized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A caninized antibody retains a similar antigenic specificity as the original antibody. However, using certain methods of caninanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Vectors

A vectors may be used to introduce the chimeric intracellular signaling molecule or the CAR into a T cell as described elsewhere herein. In one aspect, the invention includes a vector comprising a nucleic acid sequence encoding a chimeric intracellular signaling molecule and, optionally, a nucleic acid sequence encoding a bispecific antibody as described herein. In another aspect, the invention includes a vector comprising a nucleic acid sequence encoding a CAR and, optionally, a nucleic acid sequence encoding a bispecific antibody as described herein. In one embodiment, the vector comprises a plasmid vector, viral vector, retrotransposon (e.g. piggyback, sleeping beauty), site directed insertion vector (e.g. CRISPR, Zinc finger nucleases, TALEN), or suicide expression vector, or other known vector in the art.

All constructs mentioned above are capable of use with 3rd generation lentiviral vector plasmids, other viral vectors, or RNA approved for use in canine cells. In one embodiment, the vector is a viral vector, such as a lentiviral vector. In another embodiment, the vector is a RNA vector.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human and/or canine gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

Methods of introducing and expressing genes, such as the chimeric intracellular signaling molecule or the CAR, into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). Nucleic acids can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). Nucleic acids can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., canine cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the molecules described herein, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, one or more of the nucleic acid sequences described elsewhere herein are introduced by a method selected from the group consisting of transducing the population of cells, transfecting the population of cells, and electroporating the population of cells. In one embodiment, a population of cells comprises one or more of the nucleic acid sequences described herein.

In one embodiment, the nucleic acids introduced into the cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric intracellular signaling molecule and/or a bispecific antibody.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a canine cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES)

sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Some in vitro-transcribed RNA (IVT-RNA) vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In one aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Alternatively, in another aspect, the invention includes a method for generating a modified T cell comprising electroporating a population of T cells with a nucleic acid sequence encoding a chimeric intracellular signaling molecule, wherein the nucleic acid sequence comprises a nucleic acid sequence of an intracellular domain of a co-stimulatory molecule and substantially lacks an extracellular domain. In one embodiment, the nucleic acid sequence encoding a chimeric intracellular signaling molecule is electroporated into a cell. In another embodiment, a nucleic acid sequence encoding a bispecific antibody is further electroporated into the cell. In yet another embodiment, a nucleic acid sequence encoding a CAR is further electroporated into the cell.

Alternatively, the invention includes a method of metabolically enhancing a tumor specific T cell, comprising introducing a CAR into a T cell, wherein the CAR comprises an antigen binding domain, a transmembrane domain and an intracellular domain of a co-stimulatory molecule, arming the CAR T cell with a bispecific antibody, wherein the bispecific antibody binds to a target on a tumor cell and the CAR T cell, and stimulating at least one co-stimulatory molecule on the armed CAR T cell, wherein the stimulation activates the intracellular domain of the co-stimulatory molecule thereby metabolically enhancing the armed T cell. In one embodiment, introducing the CAR into the T cell comprises introducing a nucleic acid sequence encoding the CAR, such as by electroporating a mRNA encoding the CAR. In another embodiment, arming the CAR T cell comprises contacting the CAR T cell with the bispecific antibody. In yet another embodiment, arming the CAR T cell comprises introducing a nucleic acid sequence encoding the bispecific antibody, such as by electroporating a mRNA encoding the bispecific antibody. In still another embodiment, stimulating the armed CAR T cell improves cytotoxicity and resistance to immunosuppression of the armed CAR T cell when in a tumor microenvironment.

Sources of T Cells

The modified T cells may be generated from any source of T cells. In one embodiment, a source of T cells is obtained from a subject. Non-limiting examples of subjects include humans, dogs, cats, mice, rats, and transgenic species thereof. Preferably, the subject is a dog. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, a population of cells comprise the T cells of the present invention. Examples of a population of cells include, but are not limited to, peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

T cells generated by any method described herein may be expanded ex vivo. In one embodiment, T cells or a population of cells comprising T cells are cultured for expansion. Generally, T cells are expanded by contact with a surface having attached thereto an agent that stimulates a CD3/TCR complex associated signal and a ligand that stimulates a co-stimulatory molecule on the surface of the T cells.

Methods for expanding T cells are described herein. For example, the T cells can be expanded by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

The T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing one or more of the molecules described elsewhere herein into the T cells.

The culturing step as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

In one embodiment, the T cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine, canine serum or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The T cell culturing medium may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

Therapy

The modified T cells described herein are useful in a variety of treatment modalities for treatment of a number of disease states whether the T cell is modified by virtue of expression of either a chimeric intracellular signaling molecule or a CAR. Thus, irrespective of whether the T cell expresses an chimeric intracellular signaling molecule or a CAR, the T cell is referred to herein as a modified T cell. This modified T cell may be included in a composition for therapy as now described may be included in a composition for therapy.

In one aspect, the composition comprises the modified T cell comprising the chimeric intracellular signaling molecule described herein. The composition may include a pharmaceutical composition and further include a pharmaceutically acceptable carrier. A therapeutically effective amount of the pharmaceutical composition comprising the modified cells may be administered.

In one aspect, the invention includes a method of treating a disease or condition associated with enhanced immunity in a subject comprising administering to the subject a therapeutically effective amount of a pharmaceutical composition comprising the modified T cell described herein. In another aspect, the invention includes a method of treating a condition in a subject, comprising administering to the subject a therapeutically effective amount of a pharmaceutical composition comprising the modified T cell described herein. In another aspect, the invention includes a method for stimulating a T cell-mediated immune response to a target cell or tissue in a subject comprising administering to a subject a therapeutically effective amount of a pharmaceutical composition comprising the modified T cell described herein. In yet another aspect, the invention includes use of the modified T cell described herein in the manufacture of a medicament for the treatment of an immune response in a subject in need thereof. In these embodiments, the T cell comprises a chimeric intracellular signaling molecule, wherein the chimeric intracellular signaling molecule comprises an intracellular domain of a co-stimulatory molecule and substantially lacks an extracellular domain. In another embodiment, the T cell further comprises a bispecific antibody. In yet another embodiment, the T cell further comprises a CAR.

In one aspect, the invention includes a method of treating a disease or condition associated with a tumor or cancer in a subject comprising administering to the subject a therapeutically effective amount of a pharmaceutical composition comprising the modified T cell described herein that preferably comprises a CAR comprising an anti-CD20 antigen binding domain. In another aspect, the invention includes a method of treating a solid tumor in a subject, comprising administering to the subject a therapeutically effective amount of a pharmaceutical composition comprising the modified T cell described herein. In another aspect, the invention includes a method for stimulating a T cell-mediated immune response to a target tumor cell or tumor tissue in a subject comprising administering to a subject a therapeutically effective amount of a pharmaceutical composition comprising the modified T cell described herein. In yet another aspect, the invention includes use of the modified T cell described herein in the manufacture of a medicament for the treatment of a tumor or cancer in a subject in need thereof. In these embodiments, the T cell comprises a CAR and a bispecific antibody, wherein the CAR comprises an antigen binding domain, a transmembrane domain and an intracellular domain of a co-stimulatory molecule, and the bispecific antibody binds to a target on a tumor cell and the T cell.

The modified T cells as described herein can be administered to an animal, preferably a mammal, even more preferably a dog, to suppress an immune reaction, such as those common to autoimmune diseases such as diabetes, arthritis, GVHD, enhancing allograft tolerance induction, transplant rejection, and the like. In addition, the modified T cells of the present invention can be used for the treatment of any condition in which a diminished or otherwise inhibited immune response, especially a cell-mediated immune response, is desirable to treat or alleviate the disease. In one aspect, the invention includes treating a condition, such as an autoimmune disease, in a subject, comprising administering to the subject a therapeutically effective amount of a pharmaceutical composition comprising a population of the cells described herein.

The modified T cells described herein may also be used to treat inflammatory disorders. Examples of inflammatory disorders include but are not limited to, chronic and acute inflammatory disorders. Examples of inflammatory disorders include asthma, atopic allergy, allergy, atherosclerosis, glomerulonephritis, graft vs. host disease, hemolytic anemias, osteoarthritis, sepsis, stroke, transplantation of tissue and organs, vasculitis, diabetic retinopathy and ventilator induced lung injury.

The modified T cells of the present invention can be used to treat cancers. Cancers include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the cells of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

The modified T cells of the invention can be administered in dosages and routes and at times to be determined in appropriate pre-clinical and clinical experimentation and trials. Cell compositions may be administered multiple times at dosages within these ranges. Administration of the modified T cells of the invention may be combined with other methods useful to treat the desired disease or condition as determined by those of skill in the art.

The modified T cells of the invention may be autologous, allogeneic or xenogeneic with respect to the subject administered therein that is undergoing therapy.

The administration of the modified T cells of the invention may be carried out in any convenient manner known to those of skill in the art. The modified T cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the modified T cells of the invention are injected directly into a site of inflammation in the subject, a local disease site in the subject, a lymph node, an organ, a tumor, and the like.

Pharmaceutical Compositions

Pharmaceutical compositions of the present invention may comprise the modified T cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer the modified T cells to a subject and then subsequently redraw blood (or have an apheresis performed), metabolically enhance T cells therefrom according to the present invention, and reinfuse the patient with these modified T cells. This process can be carried out multiple times every few weeks. In certain embodiments, modified T cells can be obtained from blood draws from about 10 ml to about 400 ml. In certain embodiments, modified T cells are obtained from blood draws of about 20 ml, 30 ml, 40 ml, 50 ml, 60 ml, 70 ml, 80 ml, 90 ml, or 100 ml. Not to be bound by theory, using this multiple blood draw/multiple reinfusion protocol, may select out certain populations of T cells.

In certain embodiments of the present invention, T cells are modified using the methods described herein, and stimulated, activated or expanded using the methods described herein or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or treatments for PML patients. In further embodiments, the modified T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the modified T cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for canine administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way for the remainder of the disclosure.

The materials and methods employed in these experiments are now described.

Generation of Cell-Based Artificial Antigen-Presenting Cells (APCs) for Canine T Cell Expansion The human erythroleukemic cell line K562 was stably transduced with a self-inactivating lentiviral vector, pCLPS, containing the human FcγRII (CD32) and cloned by single cell sorting to produce KT32 as previously described (Maus, Nat Biotec). KT32/cCD86 cells were generated as follows: Canine CD86 was amplified from PHA and IL-2 stimulated canine PBMCs using RT-PCR with primers flanked with Bam HI and XhoI restriction sites. The resulting cDNA was cloned into the pCLPS vector. Lentivirus was generated as previously described and used to transduce KT32 cells. KT32 cells expressing high levels of cell surface canine CD86 were bulk sorted to produce KT32/cCD86. KT32/cCD86 cells were cultured in a modified version of complete RPMI medium, containing 1 mM sodium pyruvate (Mediatech, Manassas, Va.) and 30 µg/mL gentamicin (Gibco, Grand Island, N.Y.).

Generation of Anti-Canine CD3/CD28 Magnetic Beads

Agonistic mouse anti-canine CD3 (clone CA17.2A12, ABD Serotec, Raleigh, N.C.) and mouse anti-canine CD28 (clone 5B8, a generous gift of Dr. Rainer Storb) were conjugated to magnetic tosylactivated Dynabeads® (Life Technologies, Grand Island, N.Y.) according to the manufacturer's protocol. In brief, 50 µg of total antibodies per $10^8$ beads in a 1:1 ratio were incubated with activated beads for 24 hours at room temperature while blocked with sterile filtered 0.01% BSA (Sigma-Aldrich,) to prevent non-specific binding, followed by 4 hour deactivation of unused tosyl-groups at 37° C. Conjugated beads stored at $4\times10^8$/mL in 0.1% BSA w/v in DPBS (Mediatech) with 2 mM EDTA (Gibco) and 0.01% sodium azide (Amresco, Solon, Ohio) as a preservative at 4° C.

Peripheral Blood Mononuclear Cell (PBMC) Stimulation

PBMCs were isolated from the peripheral blood of a canine patient with relapsed CD20+ B cell lymphoma. Canine PBMCs were isolated by density centrifugation over Ficoll-Paque PLUS (s.g. 1.077, GE Healthcare, Uppsala, Sweden) as previously described. PBMCs were washed twice in complete medium, consisting of RPMI 1640 (Mediatech) containing 2 mM L-Glutamine, 10% heat-inactivated FBS (Atlanta Biologicals, Lawrenceville, Ga.), 10 mM HEPES (Gibco), 100U/ml penicillin and 100 µg/ml streptomycin (Gibco) and filtered through a 0.22 µM filter Stericup (Millipore, Billerica, Mass.). Live isolated cells were counted by hematocytometer using trypan blue exclusion and enriched for T cells by overnight incubation on plastic to remove adherent cells. For experiments using aAPCs for T cell activation and expansion, KT32/cCD86 cells were irradiated (10,000 rads), washed twice in complete medium, and re-suspended at $5\times10^5$ cells/mL. PBMCs were co-cultured with irradiated APCs at a 2:1 ratio. Mouse anti-canine CD3 (Serotec, Raleigh, N.C.) was added to the cultures at 0.5 ug/ml. Cells were cultured at 37° C. and 5% $CO_2$, and supplemented with 100U/mL recombinant human IL-2 (Gibco) and 10 ng/mL recombinant human IL-21 (eBioscience, San Diego, Calif.) at the time of stimulation and every other day thereafter. Cells were re-stimulated as necessary when their rate of expansion slowed, as indicated by the reduction in size and number of cell clusters, the shift from elongated to rounded cell morphology, and cell volume by Coulter Counter.

For experiments using antibody-conjugated beads, beads were washed three times with 1×DPBS and once with complete medium before co-culture with isolated and enriched PBMCs at various bead:PBMCs ratios. In all cases, cells were cultured at 37° C. and 5% $CO_2$.

Generation of Canine T Cells Modified with CAR

Modified canine T cells were generated based on K562 feeder cells genetically modified using a third generation lentiviral vector expressing canine CD86. The modified canine T cells of this invention were loaded with a commercially available anti-canine CD3 monoclonal antibody and activated and expanded. The methods for T cell activation and expansion were described elsewhere herein in the materials and methods section.

Methods of transducing activated canine T cells were optimized using a VSVg pseudotyped third generation lentiviral vector.

Three canine CAR constructs were generated: A first generation CAR and two second generation CARS. The CAR constructs contain the following components in cis: a leader sequence derived from canine CD8 alpha, an interchangeable single chain fragment variable region including a variable heavy and light chain, a hinge region derived from canine CD8 alpha, a transmembrane domain derived from canine CD8 alpha or canine CD28 and the intracellular signaling domain of canine CD3 zeta either alone or in combination with canine CD28 or canine 4-1BB.

Particularly, one second generation canine CAR construct that contains the intracellular CD28 co-stimulatory domain was generated for targeting canine CD20. The expression of the CAR was controlled by a modified human EF1A1 promoter in a third generation, replication incompetent lentiviral vector containing a central polypurine tract and a woodchuck hepatitis virus post-transcriptional regulatory/response element. VSVg pseudotyped lentivirus was generated from transfected 293T packaging cells and concentrated by centrifugation.

Canine PBMCs were activated and expanded using K562 feeder cells, transduced with human CD32 and canine CD86 and loaded with an anti-canine CD3 antibody, in the presence of recombinant human IL-2 and IL-21. Once the feeder cells were eliminated from the culture and most cultured canine PBMCs to activated, canine PBMCs were transduced with lentivirus 3-5 days post stimulation with KT32/cCD86 cells. A multiplicity of infection (MOI) of 5-20 particle forming unit (PFU) was used. The CAR consisted for a canine CD8alpha leader sequence, a scFv that targets canine CD20, canine CD8 alpha hinge, canine CD28 Tm domain and intracellular signaling domain and canine CD3 zeta (CD20-8-28-3z). Cells were cultured in rhIL-2 and rhIL-21 for 14 days. Cells were supplemented with fresh media (R10) and diluted to a concentration of 250,000-500,000 cells/ml. CAR expression and genomic integration were detected by flow cytometry and qPCR of genomic DNA with a plasmid standard curve 3-10 days post infection.

Co-Culture of Canine CAR PBMCS with Cell Lymphoma Cell Line, CLBL-1

Canine PBMCs transduced with CD20-8-28-3z canine CAR were co-cultured at a ratio of 1:1 with irradiated CLBL-1 cells for 7 days. After this time, cultured cells were re-evaluated for the expression of the canine CAR using flow cytometry. A second round of co-culture was performed at a ratio of 1:5 with irradiated CLBL-1 cells for 9 days and cultured cells were re-evaluated again for the expression of the canine CAR using flow cytometry.

Nucleotides and Amino Acids Sequences of this Invention

```
Canine CD20 scFv nucleotide sequence (SEQ ID NO: 1):
GACATCGTGCTGTCCCAGAGCCCCGCCATCCTGAGCGCCAGCCCTGGCGAGAAAG

TGACCATGACCTGCCGGGCCAGCAGCAGCCTGAGCTTCATGCACTGGTATCAGCA

GAAGCCCGGCAGCAGCCCCAAGCCCTGGATCTACGCCACCTCCAACCTGGCCTCC

GGAGTGCCCGCCAGATTCAGCGGCAGCGGCTCCGGCACCAGCTACAGCCTGACCA

TCAGCCGGGTGGAGGCCGAGGACGCCGCCACCTACTTTTGCCACCAGTGGAGCAG

CAACCCCCTGACCTTCGGAGCCGGCACCAAGCTGGAACTGAAGCGGGGCAGCACC

TCCGGCAGCGGCAAGCCTGGCAGCGGCGAGGGCAGCACCAAGGGCCAGGTGCAG

CTGAGACAGCCTGGCGCCGAGCTGGTGAAGCCAGGCGCCAGCGTGAAGTGAGCT

GCAAGGCCAGCGGCTACACCTTTACCAGCTACAACATGCACTGGGTGAAACAGAC

CCCAGGACAGGGCCTGGAATGGATCGGCGCCATCTACCCCGGCAACGGCGACACC

TCCTACAACCAGAAGTTCAAGGGCAAGGCCACCCTGACCGCCGACAAGAGCAGCA

GCACCGCCTACATGCAGCTGTCCAGCCTGACCTCCGAGGACAGCGCCGTGTACTA

CTGCGCCAGAAGCCACTACGGCAGCAACTACCTACTGGGGCCTACTGGGGC

CAGGGCACCACACTGACCGTGTCCAGC

Canine Amino acid sequence of CD20 scFv (SEQ ID NO: 2):
DIVLSQSPAILSASPGEKVTMTCRASSSLSFMHWYQQKPGSSPKPWIYATSNLASGVP

ARFSGSGSGTSYSLTISRVEAEDAATYFCHQWSSNPLTFGAGTKLELKRGSTSGSGKP

GSGEGSTKGQVQLRQPGAELVKPGASVKMSCKASGYTFTSYNMHWVKQTPGQGLE

WIGAIYPGNGDTSYNQKFKGKATLTADKSSSTAYMQLSSLTSEDSAVYYCARSHYG

SNYVDYFDYWGQGTTLTVSS

Canine CD8a Leader-CD20scFv-CD8a Hinge-CD8a Transmembrane-CD3
Zeta (SEQ ID NO: 3):
ATGGCCTCTCGGGTGACCGCCCTGCTCCTGCCGCTGGCCCTGCTGCTCCGTGCCG

CGGCGGCTAGCGACATCGTGCTGTCCCAGAGCCCCGCCATCCTGAGCGCCAGCCC

TGGCGAGAAAGTGACCATGACCTGCCGGGCCAGCAGCAGCCTGAGCTTCATGCAC

TGGTATCAGCAGAAGCCCGGCAGCAGCCCCAAGCCCTGGATCTACGCCACCTCCA
```

-continued

ACCTGGCCTCCGGAGTGCCCGCCAGATTCAGCGGCAGCGGCTCCGGCACCAGCTA

CAGCCTGACCATCAGCCGGGTGGAGGCCGAGGACGCCGCCACCTACTTTTGCCAC

CAGTGGAGCAGCAACCCCCTGACCTTCGGAGCCGGCACCAAGCTGGAACTGAAGC

GGGGCAGCACCTCCGGCAGCGGCAAGCCTGGCAGCGGCGAGGGCAGCACCAAGG

GCCAGGTGCAGCTGAGACAGCCTGGCGCCGAGCTGGTGAAGCCAGGCGCCAGCGT

GAAGATGAGCTGCAAGGCCAGCGGCTACACCTTTACCAGCTACAACATGCATGG

GTGAAACAGACCCCAGGACAGGGCCTGGAATGGATCGGCGCCATCTACCCCGGCA

ACGGCGACACCTCCTACAACCAGAAGTTCAAGGGCAAGGCCACCCTGACCGCCGA

CAAGAGCAGCAGCACCGCCTACATGCAGCTGTCCAGCCTGACCTCCGAGGACAGC

GCCGTGTACTACTGCGCCAGAAGCCACTACGGCAGCAACTACGTGGACTACTTCGA

CTACTGGGGCCAGGGCACCACACTGACCGTGTCCAGCGCTAGCCCCACTACGCCT

GCGCCGCGGCCACCCACGCGGGCGCCCACCAACGCGTCCAAGCCGGTGTCTCCG

CGCGGGGAGACCTGCCGGCCTGCGGCGGGCAGCGCAGTGAAAACAAGTGGGTTA

GACTTCGCCTGTGAAATCTACATCTGGGCACCCCTGGCTGGGACCTGCGCCGTCC

TTCTCCTGTCACTGGTCATCACCATCATCTGCCTGAGAGCAAAGTTCGGCAGGAG

CGCGGCCGCCCCCGAGCACCAGCAGGGCCCCAACCAGCTCTACAACGAGCTCAA

TCTGCGAGGAAGAGAGGAGTACGAGGTTTTGGATAAGAGACGCGGCCTGGACCC

GGAGATGGGAGGAAAGCAGAGGAAGAGGAACCCTCAGGAGGTCGTGTACAATG

CACTGCAGAAAGACAAGATGGCAGAGGCCTACAGTGAGATTGGGATAAAAAGC

GAGAACCAGCGTCGGAGAGGGAAGGGGCATGATGGCCTTTACCAGGGGCTCAGC

ACGGCCACCAAGGACACCTATGATGCCCTCCACATGCAGGCCCTGCCCCCTCGCT

GA

Canine CD8a Leader-CD20scFv-CD8a Hinge-CD28
Transmembrane-CD28-CD3 Zeta (SEQ ID NO: 4):
ATGGCCTCTCGGGTGACCGCCCTGCTCCTGCCGCTGGCCCTGCTGCTCCGTGCCG

CGGCGGCTAGCGACATCGTGCTGTCCCAGAGCCCCGCCATCCTGAGCGCCAGCCC

TGGCGAGAAAGTGACCATGACCTGCCGGGCCAGCAGCAGCCTGAGCTTCATGCAC

TGGTATCAGCAGAAGCCCGGCAGCAGCCCCAAGCCCTGGATCTACGCCACCTCCA

ACCTGGCCTCCGGAGTGCCCGCCAGATTCAGCGGCAGCGGCTCCGGCACCAGCTA

CAGCCTGACCATCAGCCGGGTGGAGGCCGAGGACGCCGCCACCTACTTTTGCCAC

CAGTGGAGCAGCAACCCCCTGACCTTCGGAGCCGGCACCAAGCTGGAACTGAAGC

GGGGCAGCACCTCCGGCAGCGGCAAGCCTGGCAGCGGCGAGGGCAGCACCAAGG

GCCAGGTGCAGCTGAGACAGCCTGGCGCCGAGCTGGTGAAGCCAGGCGCCAGCGT

GAAGATGAGCTGCAAGGCCAGCGGCTACACCTTTACCAGCTACAACATGCACTGG

GTGAAACAGACCCCAGGACAGGGCCTGGAATGGATCGGCGCCATCTACCCCGGCA

ACGGCGACACCTCCTACAACCAGAAGTTCAAGGGCAAGGCCACCCTGACCGCCGA

CAAGAGCAGCAGCACCGCCTACATGCAGCTGTCCAGCCTGACCTCCGAGGACAGC

GCCGTGTACTACTGCGCCAGAAGCCACTACGGCAGCAACTACGTGGACTACTTCGA

CTACTGGGGCCAGGGCACCACACTGACCGTGTCCAGCGCTAGCCCCACTACGCCT

GCGCCGCGGCCACCCACGCGGGCGCCCACCAACGCGTCCAAGCCGGTGTCTCCG

CGCGGGGAGACCTGCCGGCCTGCGGCGGGCAGCGCAGTGAAAACAAGTGGGTTA

```
GACTTCGCCTGTGAATTTTGGGCACTGGTGGTGGTTGGTGCAGTCCTAGTTTTCTA
TAGCTTGCTAGTAACAGTGGCTCTTTGTGCCTACTGGATAAAGAGTAAGAGTAGC
AGGATCCTTCAGAGTGACTACATGAACATGACCCCCCGGAGGCCGGGGCCCACC
CGAAGGCACTACCAACCCTATGCCCCAGCACGCGACTTTGCAGCATACCGCTCCC
TGAGAGCAAAGTTCGGCAGGAGCGCGGCCGCCCCCGAGCACCAGCAGGGTCCCA
ACCAGCTCTACAACGAGCTCAATCTGCGAGGAAGAGAGGAGTACGAGGTTTTGG
ATAAGAGACGCGGCCTGGACCCGGAGATGGGAGGAAAGCAGAGGAAGAGGAAC
CCTCAGGAGGTCGTGTACAATGCACTGCAGAAAGACAAGATGGCAGAGGCCTAC
AGTGAGATTGGGATAAAAAGCGAGAACCAGCGTCGGAGAGGGAAGGGGCATGA
TGGCCTTTACCAGGGGCTCAGCACGGCCACCAAGGACACCTATGATGCCCTCCAC
ATGCAGGCCCTGCCCCCTCGCTGA
```

Canine CD8a Leader-CD20scFv-CD8a Hinge-CD8a
Transmembrane-41BB-CD3 Zeta (SEQ ID NO: 5):
```
ATGGCCTCTCGGGTGACCGCCCTGCTCCTGCCGCTGGCCCTGCTGCTCCGTGCCG
CGGCGGCTAGCGACATCGTGCTGTCCCAGAGCCCCGCCATCCTGAGCGCCAGCCC
TGGCGAGAAAGTGACCATGACCTGCCGGGCCAGCAGCAGCCTGAGCTTCATGCAC
TGGTATCAGCAGAAGCCCGGCAGCAGCCCCAAGCCCTGGATCTACGCCACCTCCA
ACCTGGCCTCCGGAGTGCCCGCCAGATTCAGCGGCAGCGGCTCCGGCACCAGCTA
CAGCCTGACCATCAGCCGGGTGGAGGCCGAGGACGCCGCCACCTACTTTTGCCAC
CAGTGGAGCAGCAACCCCCTGACCTTCGGAGCCGGCACCAAGCTGGAACTGAAGC
GGGGCAGCACCTCCGGCAGCGGCAAGCCTGGCAGCGGCGAGGGCAGCACCAAGG
GCCAGGTGCAGCTGAGACAGCCTGGCGCCGAGCTGGTGAAGCCAGGCGCCAGCGT
GAAGATGAGCTGCAAGGCCAGCGGCTACACCTTTACCAGCTACAACATGCACTGG
GTGAAACAGACCCCAGGACAGGGCCTGGAATGGATCGGCGCCATCTACCCCGGCA
ACGGCGACACCTCCTACAACCAGAAGTTCAAGGGCAAGGCCACCCTGACCGCCGA
CAAGAGCAGCAGCACCGCCTACATGCAGCTGTCCAGCCTGACCTCCGAGGACAGC
GCCGTGTACTACTGCGCCAGAAGCCACTACGGCAGCAACTACGTGGACTACTTCGA
CTACTGGGGCCAGGGCACCACACTGACCGTGTCCAGCGCTAGCCCCACTACGCCT
GCGCCGCGGCCACCCACGCGGGCGCCCACCAACGCGTCCAAGCCGGTGTCTCCG
CGCGGGGAGACCTGCCGGCCTGCGGCGGGCAGCGCAGTGAAAACAAGTGGGTTA
GACTTCGCCTGTGAAATCTACATCTGGGCACCCCTGGCTGGGACCTGCGCCGTCC
TTCTCCTGTCACTGGTCATCACCATCATCTGCCATGGCAGAAAGAAACTCCTGTA
TTTATTCAAACAACCATTTATGAGACCAGTACAAACTGCCCAAGAGGAAGATGC
CTGTAGTTGCCGATTTCCAGAAGAAGAAGAAGGAGAATGTGACCTGAGAGCAAA
GTTCGGCAGGAGCGCGGCCGCCCCCGAGCACCAGCAGGGCCCCAACCAGCTCTA
CAACGAGCTCAATCTGCGAGGAAGAGAGGAGTACGAGGTTTTGGATAAGAGACG
CGGCCTGGACCCGGAGATGGGAGGAAAGCAGAGGAAGAGGAACCCTCAGGAGG
TCGTGTACAATGCACTGCAGAAAGACAAGATGGCAGAGGCCTACAGTGAGATTG
GGATAAAAAGCGAGAACCAGCGTCGGAGAGGGAAGGGGCATGATGGCCTTTAC
CAGGGGCTCAGCACGGCCACCAAGGACACCTATGATGCCCTCCACATGCAGGCC
CTGCCCCCTCGCTGA
```

Codon optimized Canine CD8a Leader-CD20scFv-CD8a Hinge-CD8a
Transmembrane-41BB-CD3 Zeta (SEQ ID NO: 6):
ATGGCCTCCAGAGTGACCGCCCTGCTGCTGCCCCTGGCCCTGCTGCTGAGGGCTG

CTGCCGCTAGCGACATCGTGCTGAGCCGACATCGTGCTGAGCCAGTCCCTGCTATCCT

GGAGAGAAGGTGACCATGACCTGCAGGGCCAGCTCCAGCCTGTCCTTCATGCACT

GGTACCAGCAGAAGCCTGGATCCAGCCCTAAGCCTTGGATCTACGCCACCAGCAA

CCTGGCCTCCGGAGTGCCTGCTAGATTCAGCGGATCCGGAAGCGGCACCTCCTAC

AGCCTGACCATCAGCAGGGTGGAGGCTGAGGACCTGCTACCTACTTCTGCCACC

AGTGGTCCAGCAATCCTCTGACCTTCGGCGCTGGAACCAAGCTGGAGCTGAAGAG

GGGCTCCACCAGCGGATCCGGCAAGCCTGGAAGCGGAGAGGGCTCCACCAAGGG

ACAGGTGCAGCTGAGGCAGCCTGGAGCCGAGCTGGTGAAGCCTGGCGCCAGCGTG

AAGATGTCCTGCAAGGCCAGCGGCTACACCTTCACCTCCTACAACATGCACTGGGT

GAAGCAGACCCCTGGACAGGGCCTGGAGTGGATCGGAGCCATCTACCCTGGCAAC

GGCGACACCAGCTACAATCAGAAGTTCAAGGGCAAGGCCACCCTGACCGCCGATA

AGTCCAGCTCCACCGCCTACATGCAGCTGAGCTCCCTGACCAGCGAGGACTCCGC

CCAGCGAGGACTCCGCCGTGTACTACTGCGCCAGATCGTGGACTACTTCGATT

ACTGGGGCCAGGGAACCACCCTGACCGTGAGCTCCGCTAGCCCCACCACCCCTGC

TCCTAGGCCTCCTACCAGGGCTCCTACCAATGCCTCCAAGCCCGTGAGCCCTAGA

GGAGAGACCTGCAGGCCCGCTGCTGGATCCGCCGTGAAGACCAGCGGCCTGGAT

TTCGCCTGCGAGATCTACATCTGGGCTCCCCTGGCCGGAACCTGCGCCGTGCTGC

TGCTGAGCCTGGTCATCACCATCATCTGCCACGGCCGGAAGAAGCTGCTGTACCT

GTTCAAGCAGCCCTTCATGAGGCCTGTGCAGACCGCTCAGGAGGAGGACGCTTG

CTCCTGCAGGTTCCCTGAGGAGGAGGAGGGAGAGTGCGATCTGAGGGCCAAGTT

CGGCCGCAGCGCCGCTGCTCCTGAGCACCAGCAGGGCCCTAACCAGCTGTACAA

CGAGCTGAATCTGAGGGGAAGGGAGGAGTACGAGGTGCTGGACAAGAGGAGGG

GCCTGGATCCTGAGATGGGAGGCAAGCAGAGAAAGAGGAACCCTCAGGAGGTG

GTGTACAATGCCCTGCAGAAGGACAAGATGGCCGAGGCCTACTCCGAGATCGGC

ATCAAGAGCGAGAATCAGCGCAGAAGGGGCAAGGGCCACGATGGACTGTACCA

GGGACTGTCCACCGCTACCAAGGACACCTACGATGCTCTGCACATGCAGGCCCT

GCCTCCTAGGTGA

Nucleotide Sequence for pDA.CD20-hCD3z (SEQ ID NO: 7)
CD8a Leader-CD20scFv-CD8a Hinge-CD8a Transmembrane(TM)-CD3 Zeta
The color coding in the sequence below corresponds to the following:
CD8a leader (human); CD20scFv(mouse); CD8a hinge(human); CD8a
TM(human); and CD3 Zeta(human)
ATGGCCTTACCAGTGACCGCCTTGCTCCTGCCGCTGGCCTTGCTGCTCCACG

CCGCCAGGCCGGGATCAGCCGGATCC*GACATCGTGCTGTCCCAGAGCCCCGCCA*

*TCCTGAGCGCCAGCCCTGGCGAGAAAGTGACCATGACCTGCCGGGCCAGCAGCAG*

*CCTGAGCTTCATGCACTGGTATCAGCAGAAGCCCGGCAGCAGCCCCAAGCCCTGG*

*ATCTACGCCACCTCCAACCTGGCCTCCGGAGTGCCCGCCAGATTCAGCGGCAGCG*

*GCTCCGGCACCAGCTACAGCCTGACCATCAGCCGGGTGGAGGCCGAGGACGCCGC*

*CACCTACTTTTGCCACCAGTGGAGCAGCAACCCCCTGACCTTCGGAGCCGGCACCA*

*AGCTGGAACTGAAGCGGGGCAGCACCTCCGGCAGCGGCAAGCCTGGCAGCGGCG*

*AGGGCAGCACCAAGGGCCAGGTGCAGCTGAGACAGCCTGGCGCCGAGCTGGTGA*

-continued

```
AGCCAGGCGCCAGCGTGAAGATGAGCTGCAAGGCCAGCGGCTACACCTTTACCAG

CTACAACATGCACTGGGTGAAACAGACCCCAGGACAGGGCCTGGAATGGATCGGC

GCCATCTACCCCGGCAACGGCGACACCTCCTACAACCAGAAGTTCAAGGGCAAGG

CCACCCTGACCGCCGACAAGAGCAGCAGCACCGCCTACATGCAGCTGTCCAGCCT

GACCTCCGAGGACAGCGCCGTGTACTACTGCGCCAGAAGCCACTACGGCAGCAAC

TACGTGGACTACTTCGACTACTGGGGCCAGGGCACCACACTGACCGTGTCCAGCG

CTAGCACCACGACGCCAGCGCCGCGACCACCAACACCGGCGCCCACCATCGCGTCG

CAGCCCCTGTCCCTGCGCCCAGAGGCGTGCCGGCCAGCGGCGGGGGGCGCAGTGC

ACACGAGGGGCTGGACTTCGCCTGTGATATCTACATCTGGGCGCCCTTGGCCG

GGACTTGTGGGGTCCTTCTCCTGTCACTGGTTATCACCCTTTACTGCAGAGT

GAAGTTCAGCAGGAGCGCAGACGCCCCGCGTACCAGCAGGGCCAGAACCAGCT

CTATAACGAGCTCAATCTAGGACGAAGAGAGGAGTACGATGTTTTGGACAAGAG

ACGTGGCCGGGACCCTGAGATGGGGGGAAAGCCGAGAAGGAAGAACCCTCAGG

AAGGCCTGTACAATGAACTGCAGAAAGATAAGATGGCGGAGGCCTACAGTGAGA

TTGGGATGAAAGGCGAGCGCCGGAGGGGCAAGGGGCACGATGGCCTTTACCAGG

GTCTCAGTACAGCCACCAAGGACACCTACGACGCCCTTCACATGCAGGCCCTGCC

CCCTCGCTAA
```

The results of the experiments are now described.

Example 1: Efficacy of CD20-Specific CAR T Cells In Vitro

CD20 is known to be a marker present on most B-cell cancers, and absent on otherwise similar appearing T-cell cancers. This feature makes CD20 particularly useful in diagnosing and/or treating conditions such as B-cell lymphomas and leukemias.

Figure 1B:
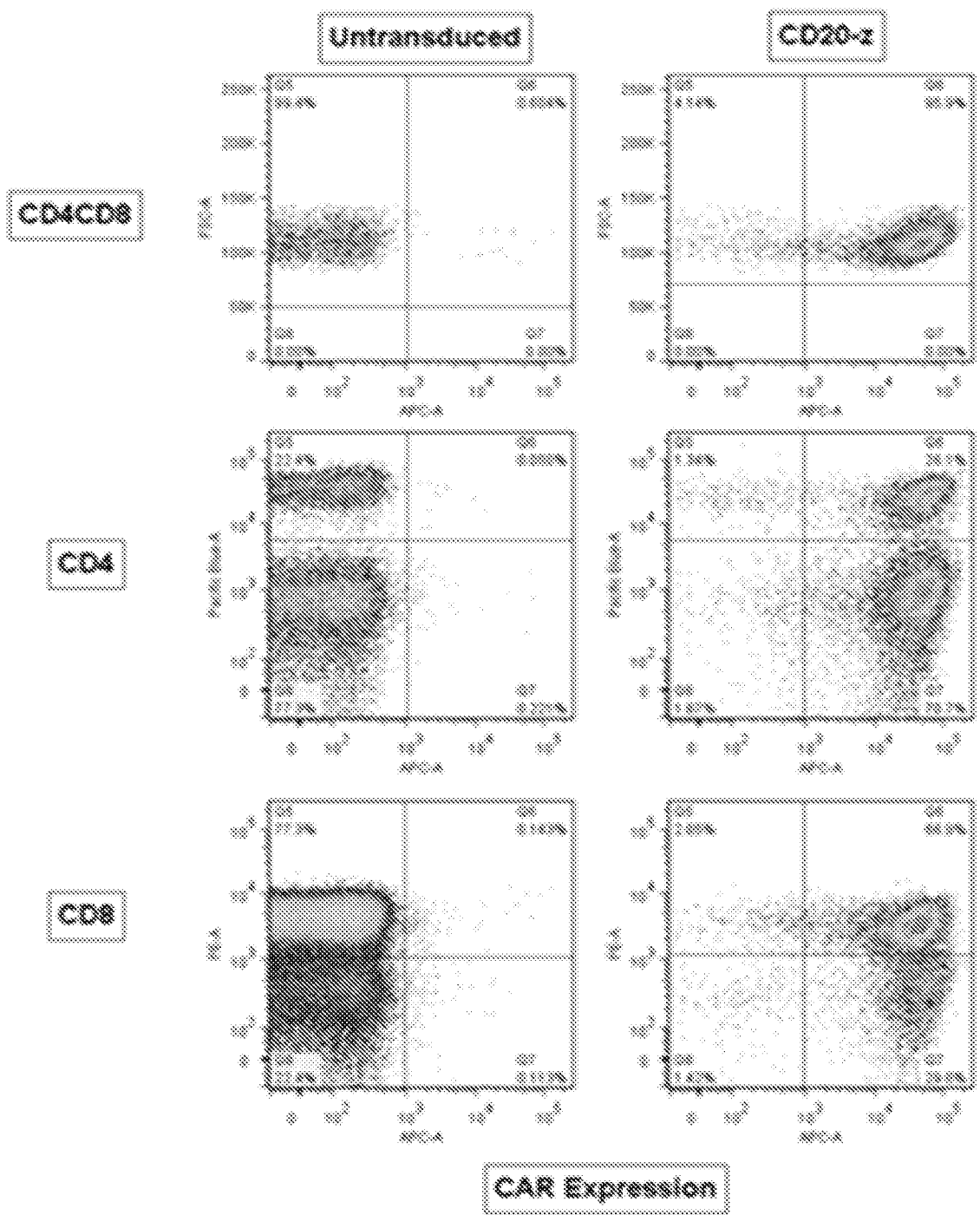
Figure 1C:
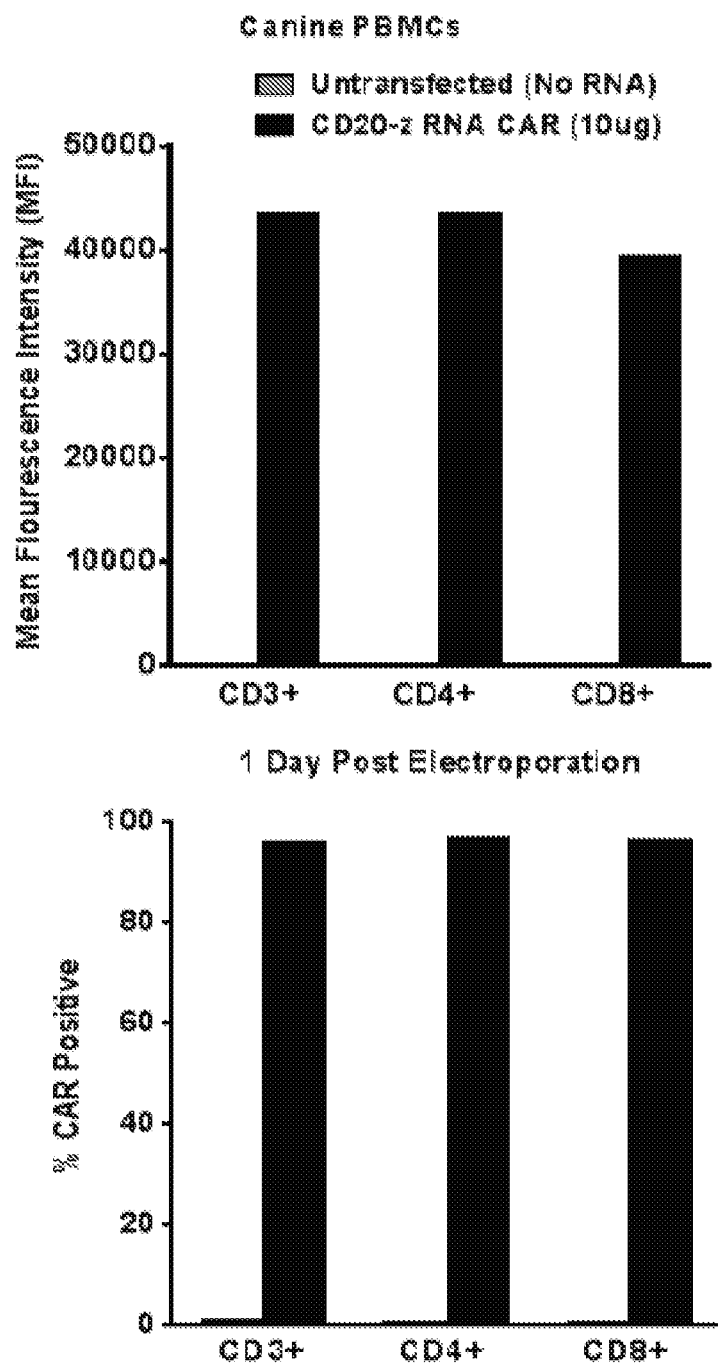
Figure 2A:
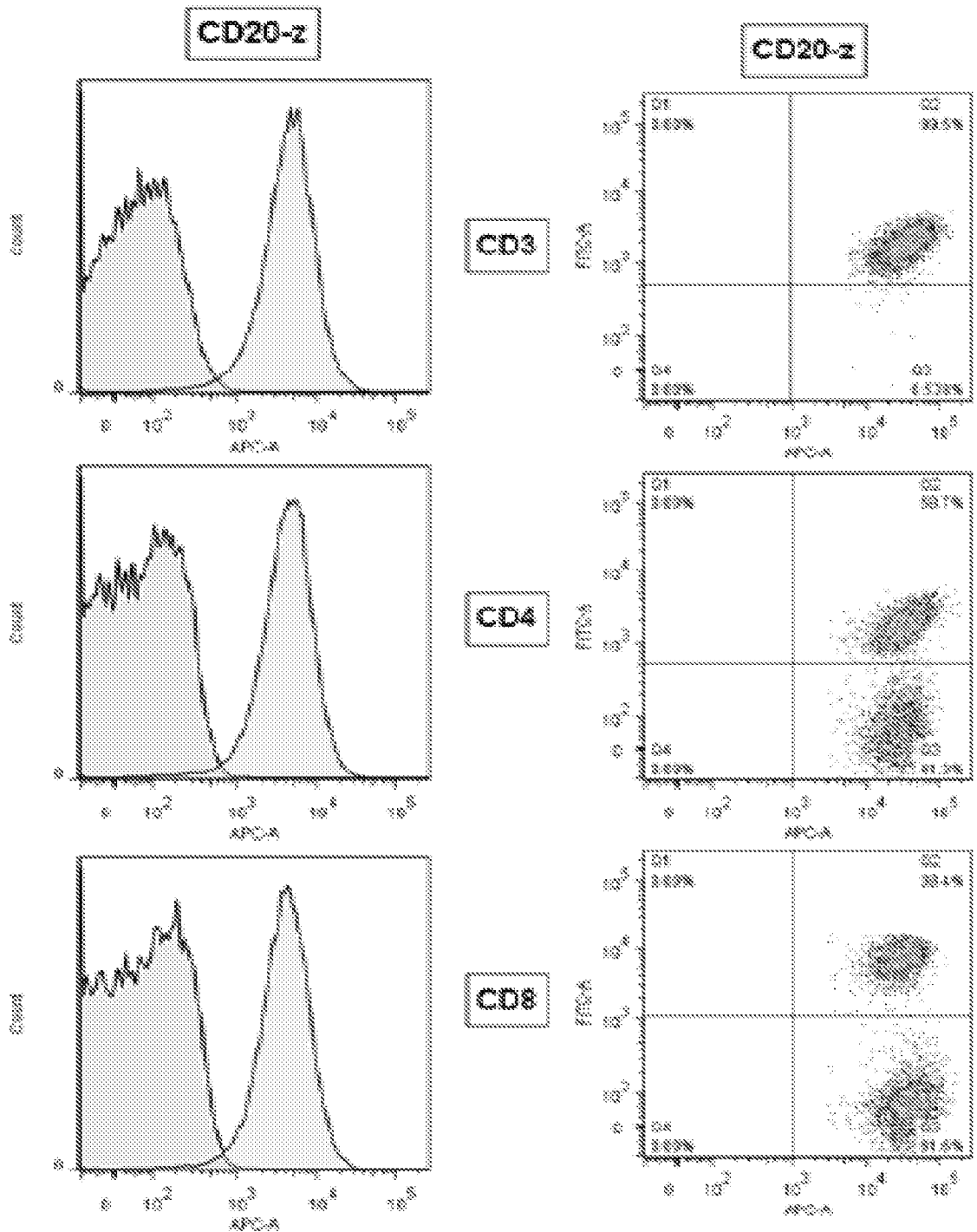
FIGS. 2A-2B are a series of graphs showing the persistence of high expression of CD20-z RNA CAR in nearly 100% of human CD3$^+$, CD4$^+$ and CD8$^+$ T cells (FIG. 2A) and in canine PBMC (FIG. 2B) populations 72 hours post electroporation.
Figure 2B:
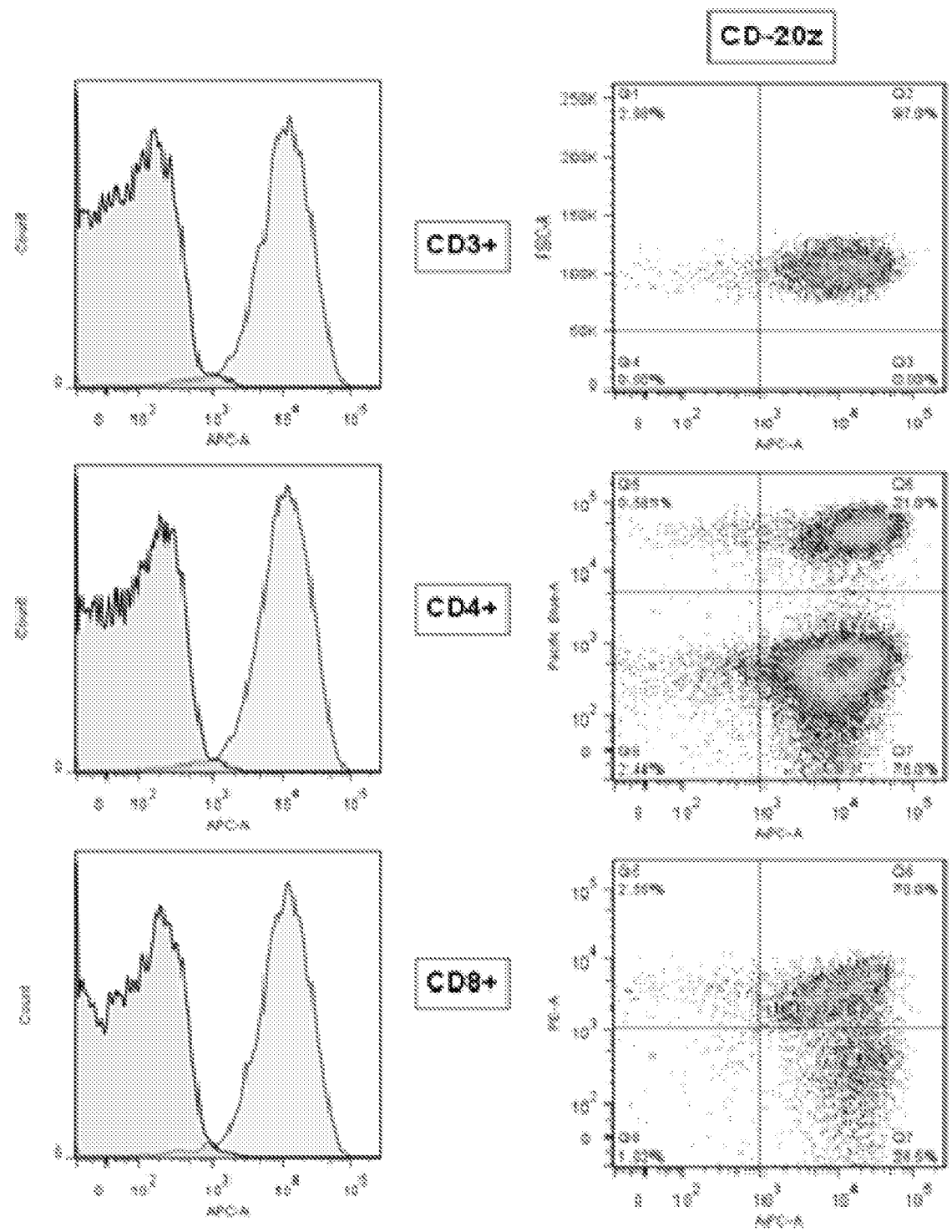
Figure 3:
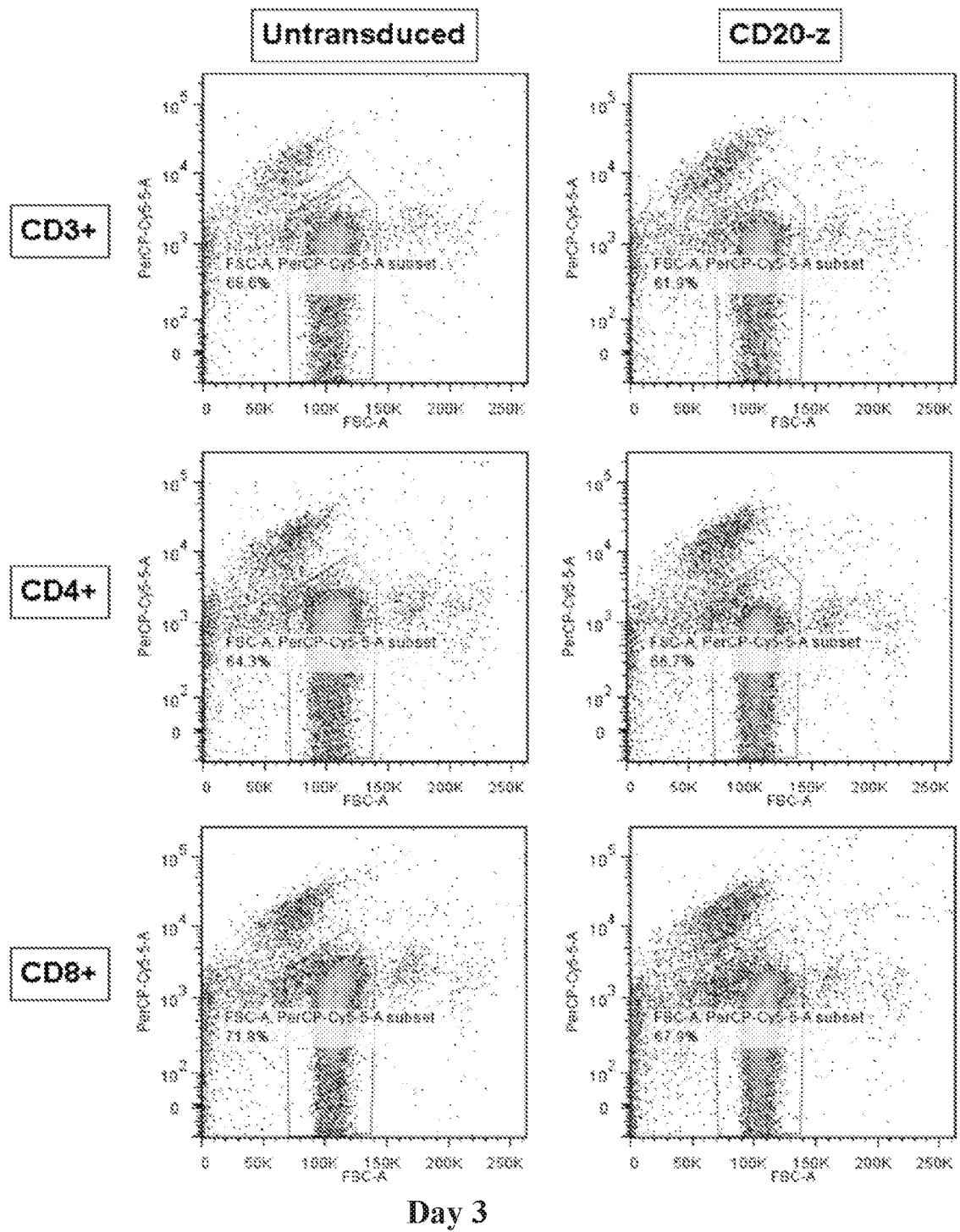
FIG. 3 is a series of graphs and histograms depicting the viability of human CD3$^+$, CD4$^+$ and CD8$^+$ T cell populations 72 hours after electroporation with the CD20-z RNA CAR (10 ug of RNA).
Figure 4:
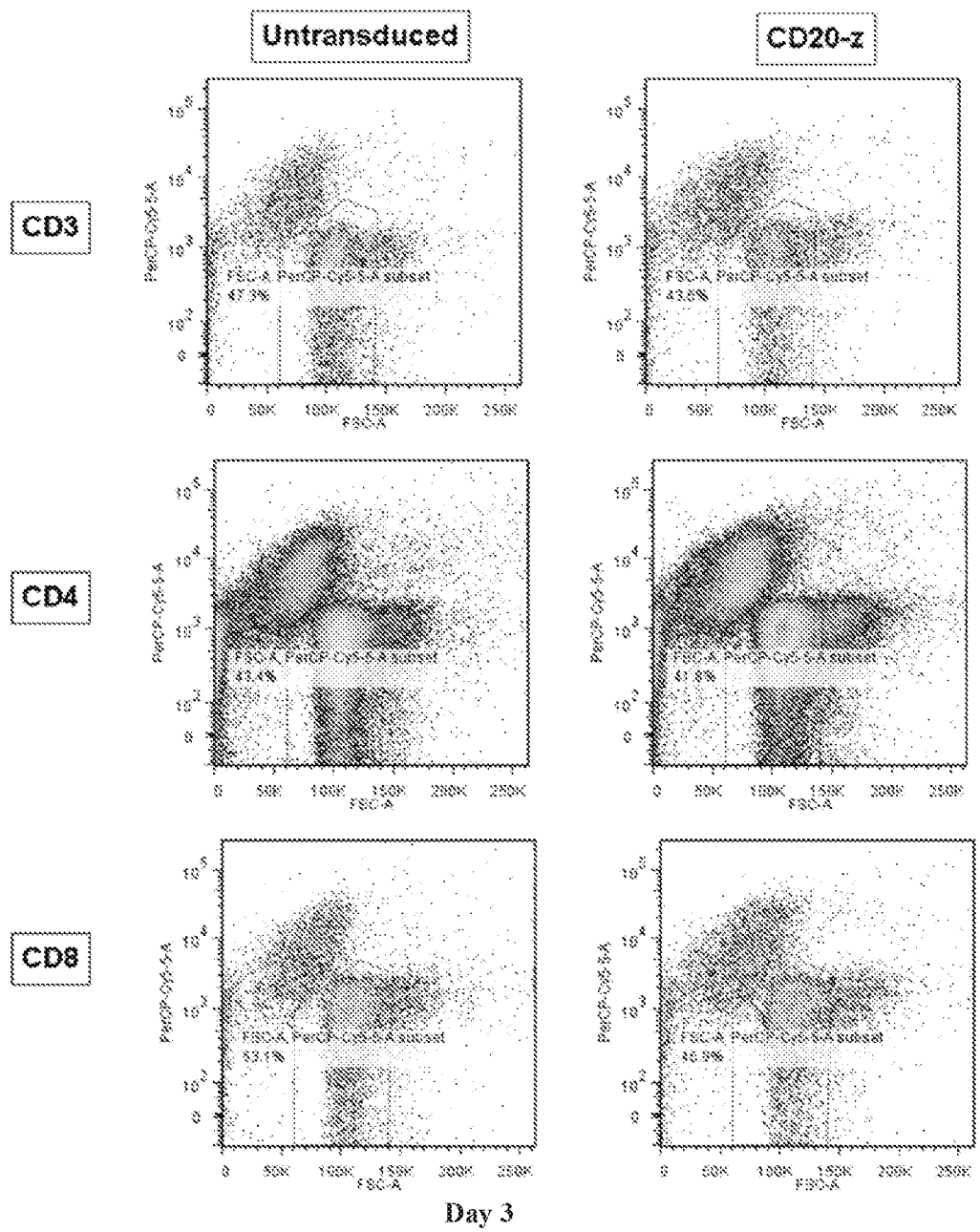
FIG. 4 is a series of graphs and histograms depicting the viability of electroporated CD20-z RNA CAR expression in CD3$^+$, CD4$^+$ and CD8$^+$ canine PBMC populations 72 hours post electroporation (10 ug of RNA).
Figure 5A:
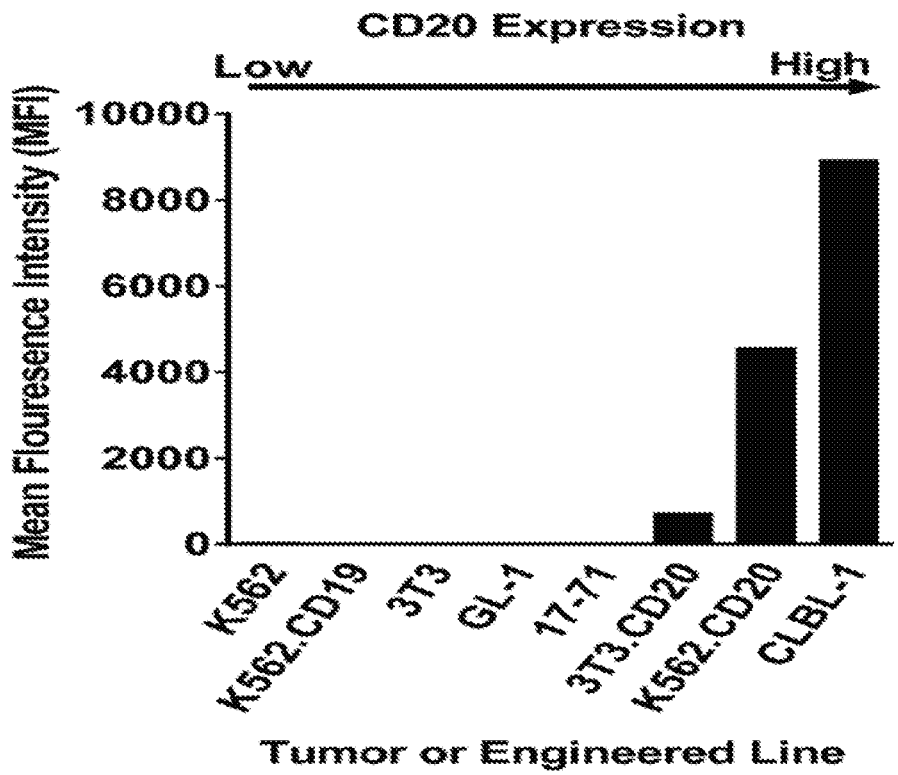
FIGS. 5A-5B are series of graphs and histograms depicting the level of CD20 expression on canine B cell lymphoma/leukemia cell lines (GL-1, 17-71 and CLBL-1) and on engineered cell lines that express canine CD20 (3T3-CD20, K562-CD20). K562: human myelogenous leukemia; K562.CD19 or K562.CD20: engineered to express human CD19 or canine CD20; 3T3: mouse embryonic fibroblast; 3T3.CD20: engineered to express canine CD20; GL-1: canine B-cell lymphoma; 17-71: canine B-cell lymphoma; CLBL-1: canine B-cell lymphoma.
Figure 5B:
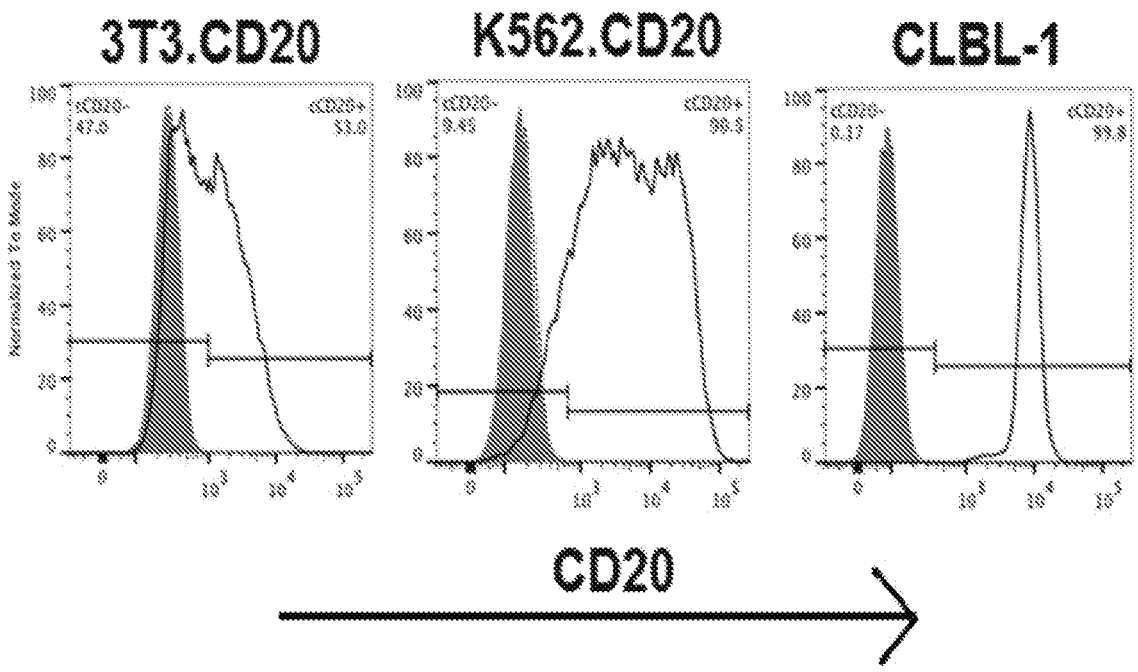

A high and persistent expression of the CD20-z CAR in $CD3^+$, $CD4^+$ and $CD8^+$ human T cells and canine PBMC populations was successfully demonstrated at 24 hours (FIGS. 1A-1C) and 72 hours (FIGS. 2A-2B, FIG. 3 and FIG. 4) post electroporation. In addition, both human and canine cells showed high viability at both time points post electroporation. The tumor and engineered cell lines expressing CD20 of this invention are presented in FIGS. 5A-5B.

Figure 6A:
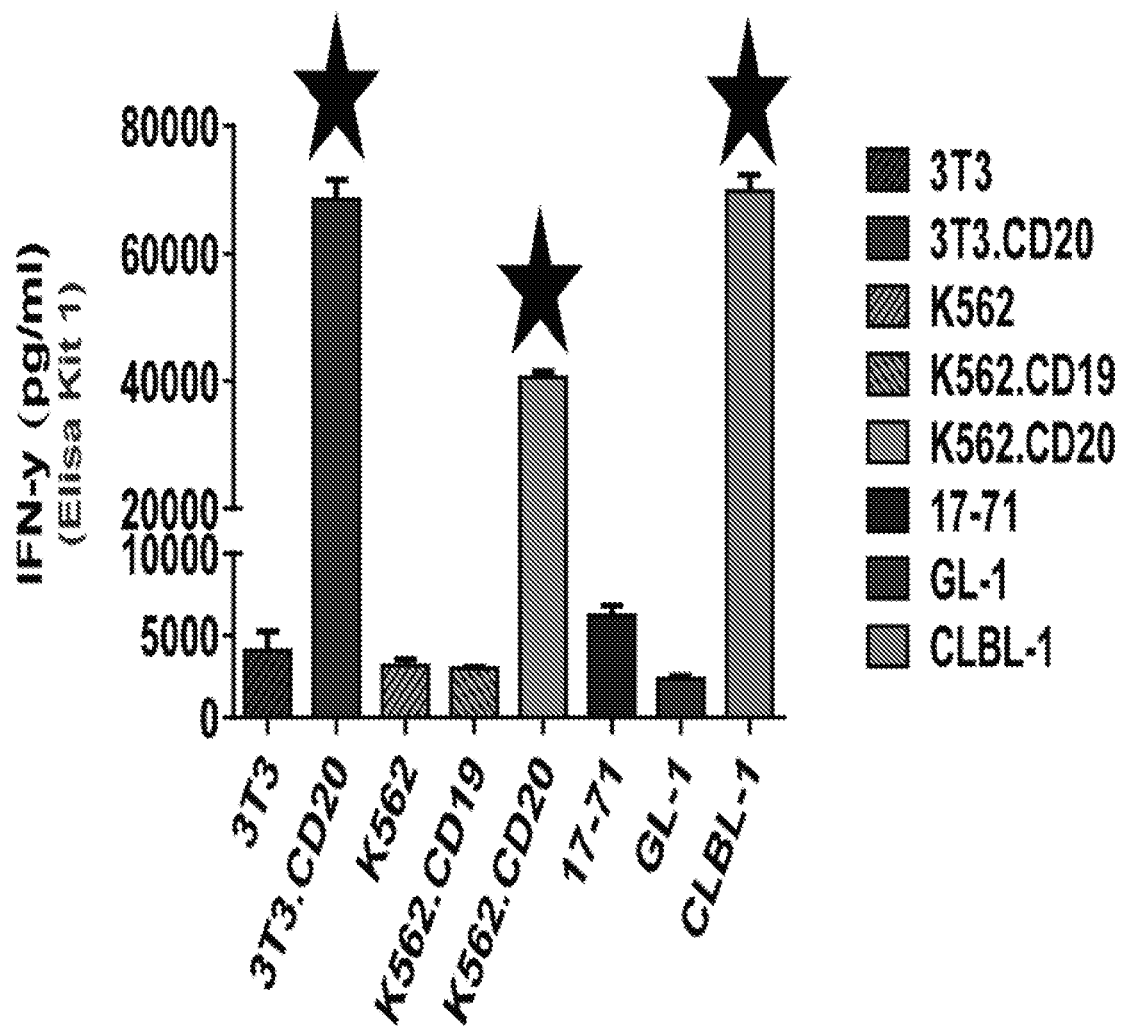
FIGS. 6A-6B are series of histograms demonstrating that CD20-z RNA CAR displayed potent effector function in canine PBMCs. IFNγ production by CD20-z RNA transfected canine PBMCs (10 ug RNA) 24 hours after co-culture at a 1:1 ratio ($10^5$ T cells: $10^5$ T cell tumor) was measured with R&D Systems Quantikine ELISA (FIG. 6A). Results from FIG. 6A were similar to FIG. 6B, except that background OD was substantially higher in FIG. 6B as indicated by CD20-z PBMCs displaying spontaneous (no tumor) cytokine production and by PBMC/tumor-free (control) displaying OD values of approximately 0.4 which were subtracted from all samples prior to analysis. In addition, ultrapure BSA appeared to be a critical requirement. Despite the significantly lower cost of the DuoSet Development System, the Quantikine ELISA provided a more rapid and sensitive method of detection.
Figure 6B:
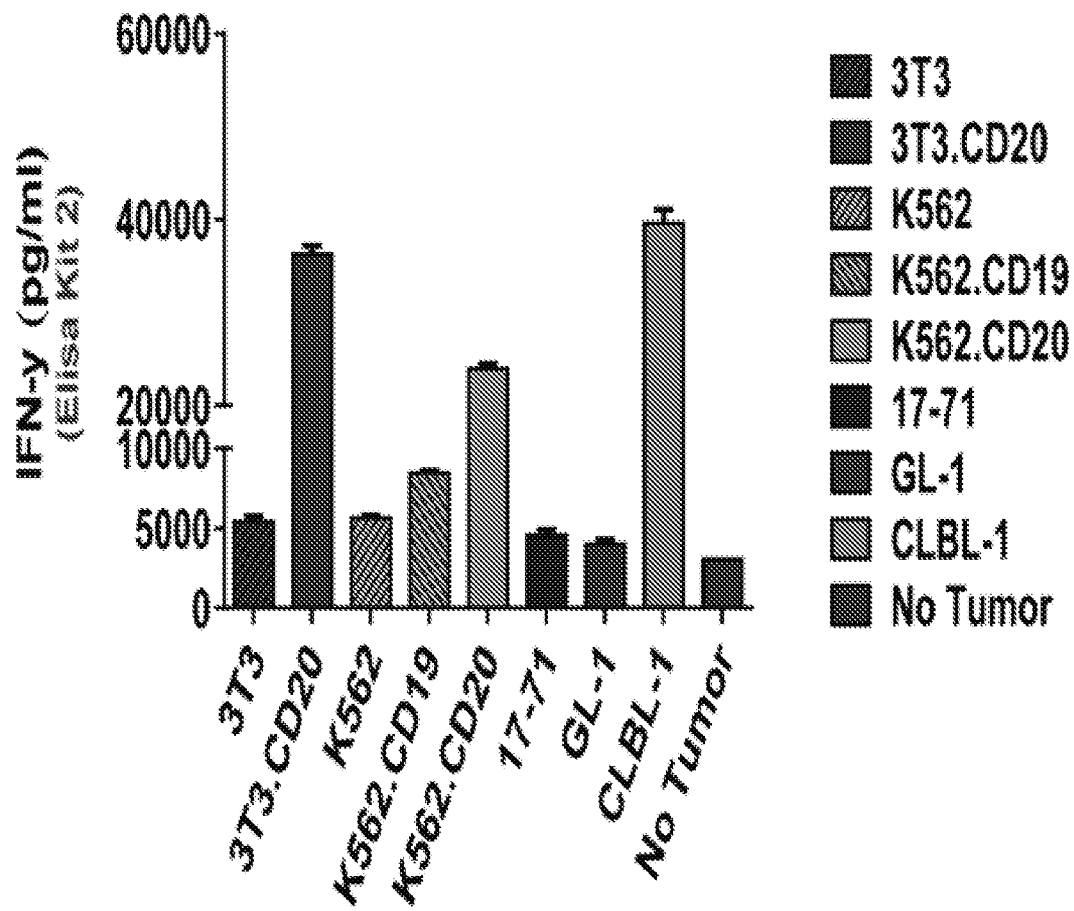

24 hours after co-culture, at a 1:1 ratio, of modified T cells and CD20 tumor cells, the IFNγ production by CD20-z RNA transfected canine PBMCs was measured. These results clearly showed that CD20-z RNA CAR displayed potent effector function in canine PBMCs (FIGS. 6A-6B).

Figure 7A:
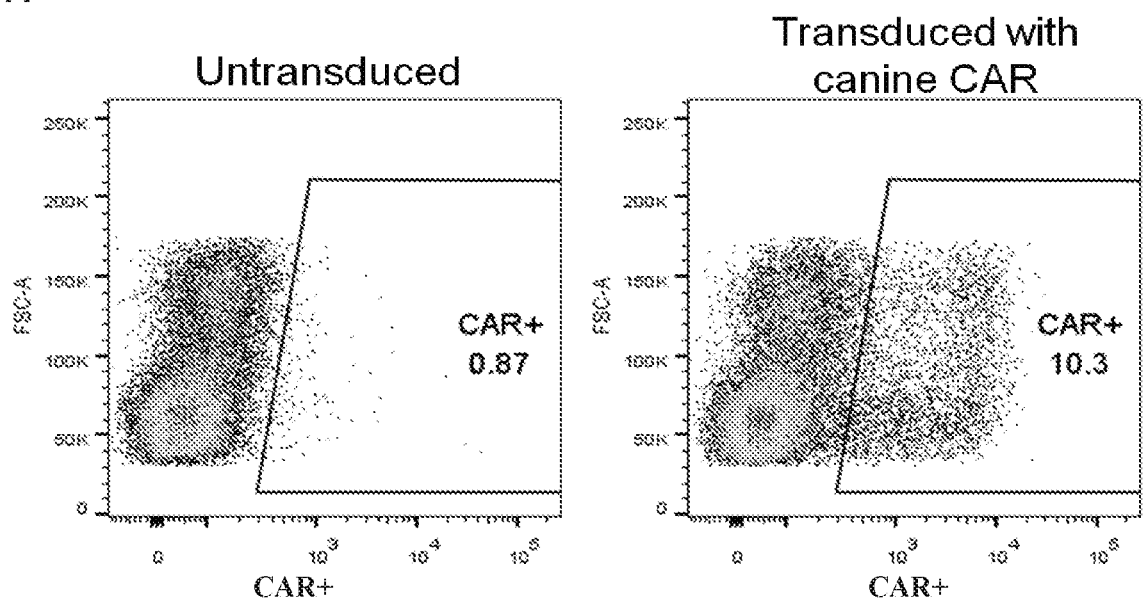
FIGS. 7A-7B are series of graphs depicting canine PBCMs transduced with lentivirus containing a second generation CD20-8-28-z canine CAR.
Figure 7B:
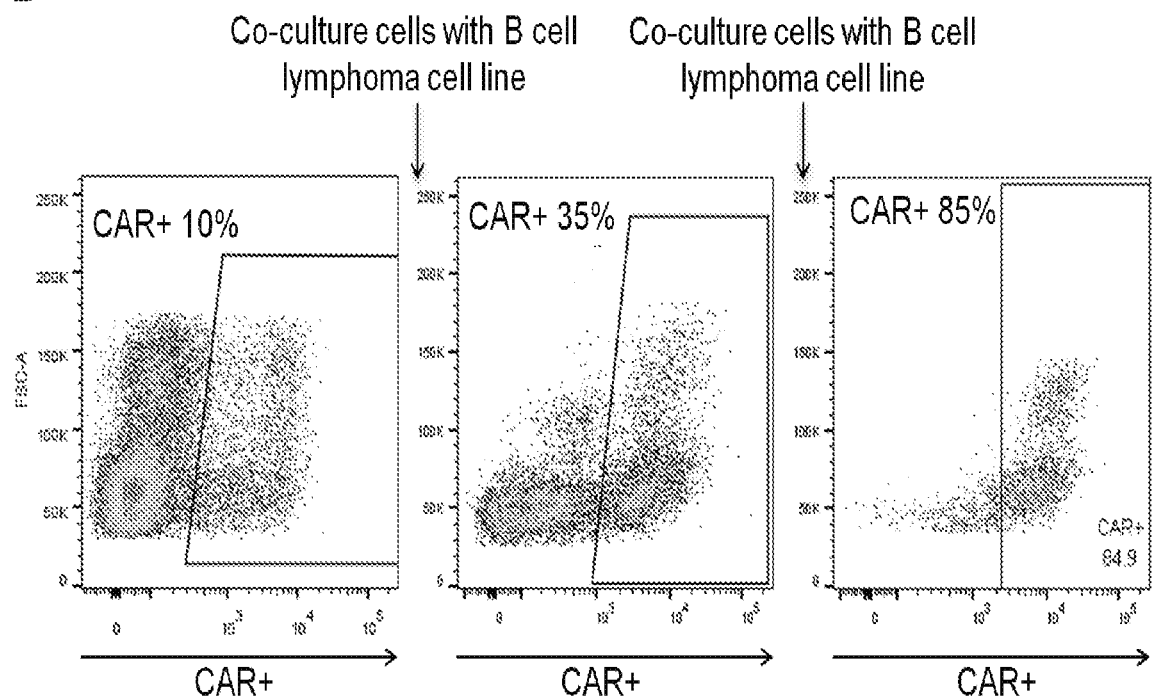
Figure 8:
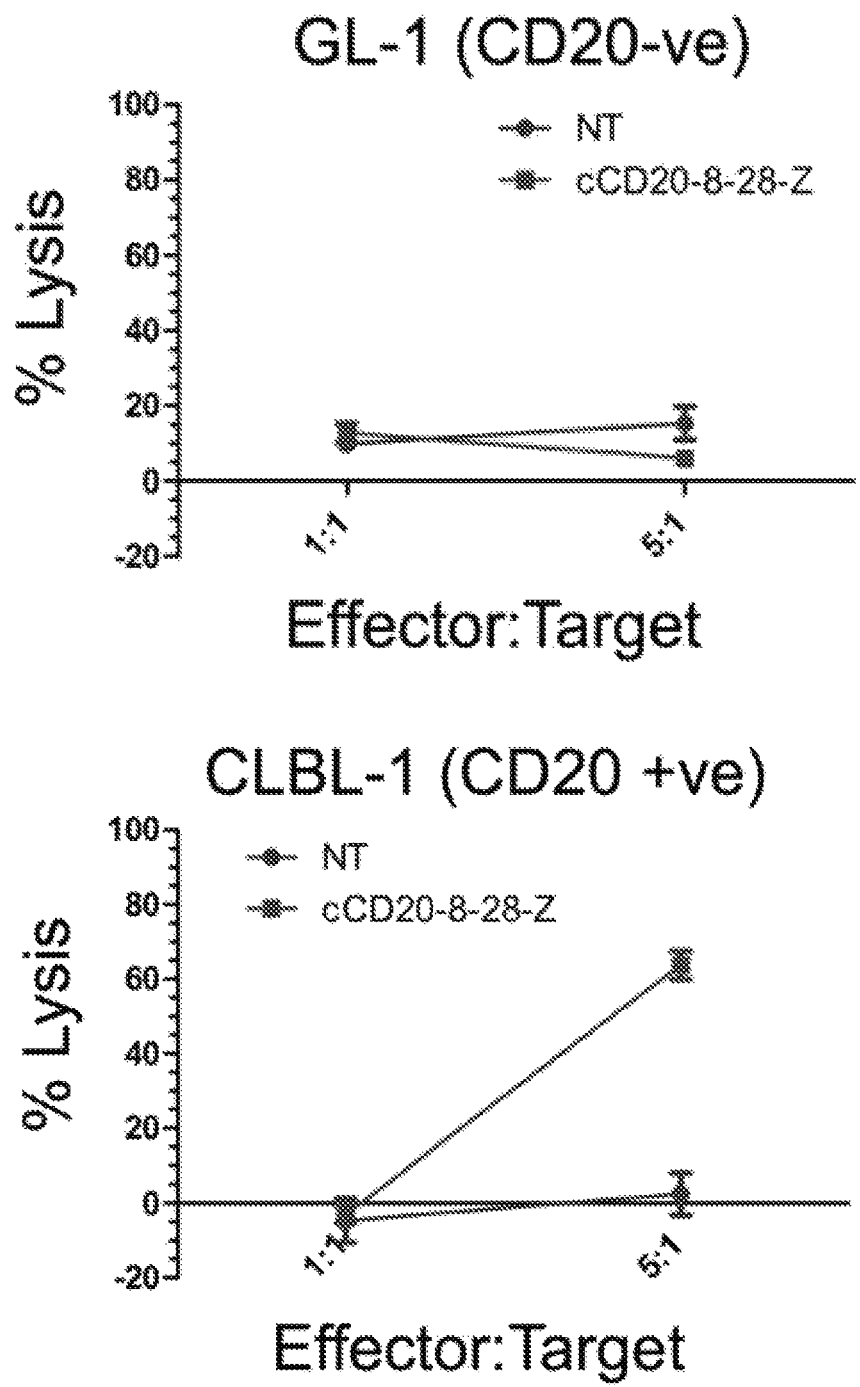
FIG. 8 is a series of graphs depicting canine PBMCs genetically modified to express a canine CD20 specific second generation CAR. This figure demonstrates an antigen-specific killing of a CD20+ B cell lymphoma cell line (CLBL-1) but not a CD20− canine B cell line (GL-1).

Additional experiments with canine PBCMs transduced with lentivirus containing a second generation CD20-8-28-3z canine CAR suggested an antigen-specific expansion after one round of co-culture with the canine CD20+ B cell lymphoma cell line, CLBL-1 and clearly demonstrated a significant expansion (approximately 85%) of the antigen specific CAR+ T cell following 2 rounds of co-culture with the CLBL-1 (FIGS. 7A-7B). Subsequently, canine T cells transduced with the canine CD20 targeting CAR (resulting in 10% CAR+ cells) were co-cultured with either a canine CD20– B cell line GL-1 (GL-1) or a CD20+ B cell lymphoma cell line (CLBL-1) at total T cell effector:Target ratios of 5:1 and 1:1 (CAR+ T cell: Target 0.5:1 and 0.1:1). After 24 hours, the percentage of lysis was calculated. The results showed that canine PBMCs genetically modified to express a canine CD20 specific second generation CAR exhibit high antigen-specificity and had the ability of killing CD20+ B cell lymphoma cell line (CLBL-1) but not a CD20-canine B cell line (GL-1) (FIG. 8).

In the present invention, canine T cells transduced to express a CD20 targeting second generation CAR were shown to express the CAR on the cell surface and signal through the CAR upon engagement with CD20. CAR signaling led to T cell activation, proliferation, cytokine production and cytotoxic function. Co-culture of CD20 CAR positive T cells ($CAR^+$ T cells) with a canine B cell lymphoma line led to rapid expansion of $CAR^+$ T cells and elimination of malignant B cell in vitro.

The results presented herein demonstrated that canine T cells expressing CAR, by using gene expression vector systems (RNA electroporation, lentivirus or retrovirus), were able to mediate antigen-specific immune responses against cancer cells in vitro. These results provide great support for an effective CAR T cell therapy in dogs with $CD20^+$ malignancies.

A current ongoing clinical trial is exploring the safety and feasibility of using genetically modified T cells expressing CD20 targeting CARs to treat dogs with spontaneous relapsed, refractory B cell lymphoma.

Example 2: Evidence of CD20-Specific CAR T Cell Activity In Vivo

Based on the in vitro data demonstrating that canine T cells can be genetically modified to express a CD20-specific CAR, and can proliferate and kill CD20+ target cells upon engagement of this CAR, the safety and efficacy of a lentiviral, second generation CD20-CD28-zeta CAR (SEQ ID NO: 4) in a dog with relapsed B cell lymphoma was evaluated.

A five year old, female spayed Golden Retriever previously diagnosed with B cell lymphoma was presented to the clinic. The canine patient had received standard of care chemotherapy and had achieved a short lived, clinical remission. At the time of presentation, the dog had generalized lymphadenopathy and relapse was confirmed by cytology and flow cytometry. Blood was drawn to generate an autologous CAR T cell product. The dog received a single dose of L-asparaginase at that time. After 14 days, the ex-vivo expanded T cell product (CD20-CD28-zeta, SEQ ID NO: 4) was sufficient to provide 33.47×10⁶ total T cells/kg with a CAR T cell dose of 6.6×10⁵ CAR+ T cells/kg. The dog received 3 days of cyclophosphamide as a pre-conditioning regime prior to CAR T cell administration. On the day of infusion, the dog was pre-medicated with ondansetron and diphenhydramine prior to infusion. The ex-vivo expanded T cells were administered over 15 mins. Transient nausea was observed immediately following administration but this was short-lived. The dog was re-examined at frequent intervals thereafter at which time blood was drawn and lymph node aspirates were taken to evaluate tumor burden and cell phenotypes (FIG. 9).

Over the course of 36 days, the percentage of malignant B cells (CD79a+ cells) decreased and the percentage of T cells (CD5+ cells) increased in the node to reverse the abnormal B:T ratio of 2.2:1 back to a more normal ratio of 0.6:1 (FIG. 9, upper panel). At the point of maximum effect (day 36) in the lymph node, the percentage of CD8+ T cells increased by almost 50%, suggesting expansion of cytotoxic T cells in the periphery, a feature that is seen in human patients treated with CAR T cells (FIG. 9, lower panel). The dog continued to respond well clinically and survived for a total of 167 days following a single administration of CAR T cells. With standard of care chemotherapy, which included treatment every week for 5 months, the dog was in remission for 237 days.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid sequence encoding a chimeric antigen receptor (CAR) comprising a canine CD20 antigen binding domain, a transmembrane domain, a costimulatory signaling region, and a CD3 zeta signaling domain, wherein the canine CD20 antigen binding domain comprises an anti-CD20 single chain variable fragment (scFv) comprising SEQ ID NO: 2.

2. The isolated nucleic acid sequence of claim 1, wherein the isolated nucleic acid sequence comprises a sequence selected from the group consisting of SEQ ID NOs: 3-6.

3. The isolated nucleic acid sequence of claim 1, wherein the canine CD20 antigen binding domain binds to CD20 expressed by tumor cells and/or tumor vasculature.

4. The isolated nucleic acid sequence of claim 3, wherein the tumor cells are from a cancer selected from the group consisting of lymphoma, Hodgkin's lymphoma, non-Hodgkin's lymphoma, lymph nodes cancer, bone marrow cancer, liver cancer, spleen cancer, ovarian cancer, renal cell carcinoma, bladder cancer, kidney cancer, testicular cancer, prostate cancer, breast cancer, colon cancer, pancreatic cancer, lung cancer, stomach cancer, eye cancer, skin cancer and any combination thereof.

5. The isolated nucleic acid sequence of claim 4, wherein the cancer is Hodgkin's lymphoma or non-Hodgkin's lymphoma.

6. The isolated nucleic acid sequence of claim 1, wherein the costimulatory signaling region comprises an intracellular domain of a costimulatory molecule selected from the group consisting of CD8, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

7. The isolated nucleic acid sequence of claim 1, wherein the nucleic acid sequence is selected from the group consisting of a DNA and an mRNA.

8. The isolated nucleic acid sequence of claim 1, wherein the nucleic acid sequence encoding the CAR is codon optimized to favor an increase in gene expression, translation efficiency and/or protein expression.

9. A vector comprising the isolated nucleic acid sequence of claim 1.

10. A chimeric antigen receptor (CAR) comprising a canine CD20 antigen binding domain, a transmembrane domain, a costimulatory signaling region, and a CD3 zeta signaling domain, wherein the canine CD20 antigen binding domain comprises an anti-CD20 single-chain variable fragment (scFv) comprising SEQ ID NO: 2.

11. The CAR of claim 10, wherein the canine CD20 antigen binding domain binds to CD20 expressed by tumor cells and/or tumor vasculature.

12. The CAR of claim 11, wherein the tumor cells are from a cancer selected from the group consisting of lymphoma, Hodgkin's lymphoma, non-Hodgkin's lymphoma, lymph nodes cancer, bone marrow cancer, liver cancer, spleen cancer, renal cell carcinoma, bladder cancer, kidney cancer, testicular cancer, prostate cancer, breast cancer, colon cancer, pancreatic cancer, lung cancer, stomach cancer, eye cancer, skin cancer and any combination thereof.

13. The CAR of claim 12, wherein the cancer is Hodgkin's lymphoma or non-Hodgkin's lymphoma.

14. The CAR of claim 10, wherein the costimulatory signaling region comprises an intracellular domain of a costimulatory molecule selected from the group consisting of CD8, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

15. The CAR of claim 14, wherein the costimulatory signaling region comprises an intracellular domain of CD28, and further wherein the CD28 is canine CD28.

16. The CAR of claim 14, wherein the costimulatory signaling region comprises an intracellular domain of 4-1BB, and further wherein the 4-1BB is canine 4-1BB.

17. The CAR of claim 14, wherein the CD3 zeta signaling domain is a canine CD3 zeta signaling domain.

18. The CAR of claim 10, wherein the CAR is encoded by a codon optimized sequence to favor an increase in gene expression, translation efficiency and/or protein expression.

19. The CAR of claim 10, further comprising a canine CD8α leader sequence.

20. The CAR of claim 10, further comprising a canine CD8α hinge.

21. The CAR of claim 10, wherein the transmembrane domain is selected from a canine CD8a transmembrane domain and a canine CD28 transmembrane domain.

22. A cell comprising the CAR of claim 10.

23. A chimeric antigen receptor (CAR) comprising a canine CD20 antigen binding domain, a transmembrane domain, a costimulatory signaling region, and a CD3 zeta signaling domain, wherein the CAR is encoded by a sequence selected from the group consisting of SEQ ID NOs: 3-6.

24. A modified cell comprising a nucleic acid sequence encoding a chimeric antigen receptor (CAR) comprising a canine CD20 antigen binding domain, a transmembrane domain, a costimulatory signaling region, and a CD3 zeta signaling domain, wherein the canine CD20 antigen binding domain comprises an anti-CD20 single-chain variable fragment (scFv) comprising SEQ ID NO: 2.

25. The modified cell of claim 24, wherein the canine CD20 antigen binding domain binds to CD20 expressed by tumor cells and/or tumor vasculature.

26. The modified cell of claim 25, wherein the tumor cells are from a cancer selected from the group consisting of lymphoma, Hodgkin's lymphoma, non-Hodgkin's lymphoma, lymph nodes cancer, bone marrow cancer, liver cancer, spleen cancer, ovarian cancer, renal cell carcinoma, bladder cancer, kidney cancer, testicular cancer, prostate cancer, breast cancer, colon cancer, pancreatic cancer, lung cancer, stomach cancer, eye cancer, skin cancer and any combination thereof.

27. The modified cell of claim 26, wherein the cancer is Hodgkin's lymphoma or non-Hodgkin's lymphoma.

28. The modified cell of claim 24, wherein the cell is selected from the group consisting of a T cell, a natural killer (NK) cell, a cytotoxic T lymphocyte (CTL), and a regulatory T cell.

29. The modified cell of claim 24, wherein the nucleic acid sequence is selected from the group consisting of a DNA and an mRNA.

30. The modified cell of claim 24, wherein the nucleic acid sequence is introduced into the cell by at least one procedure selected from the group consisting of electroporation, usage of a lentivirus, usage of a retrovirus and a chemical-based transfection.

31. A composition comprising the modified cell of claim 24.

32. A pharmaceutical composition comprising the modified cell of claim 24 and a pharmaceutically acceptable carrier.

33. A method for stimulating a T cell-mediated immune response in a canine, the method comprising administering to the canine an effective amount of a modified cell that expresses a chimeric antigen receptor comprising a canine CD20 antigen binding domain, a transmembrane domain, a costimulatory signaling region, and a CD3 zeta signaling domain, wherein the canine CD20 antigen binding domain comprises an anti-CD20 single-chain variable fragment (scFv) comprising SEQ ID NO: 2.

34. A method of treating a canine with disease or condition, the method comprising administering to the canine a modified canine T cell that expresses a chimeric antigen receptor comprising a canine CD20 antigen binding domain, a transmembrane domain, a costimulatory signaling region, and a CD3 zeta signaling domain, wherein the canine CD20 antigen binding domain comprises an anti-CD20 single-chain variable fragment (scFv) comprising SEQ ID NO: 2, and wherein the disease or condition is a CD20+cancer.

35. The method of claim 34, wherein the cancer is selected from the group consisting of lymphoma, Hodgkin's lymphoma, non-Hodgkin's lymphoma, lymph nodes cancer, bone marrow cancer, liver cancer, spleen cancer, ovarian cancer, renal cell carcinoma, bladder cancer, kidney cancer, testicular cancer, prostate cancer, breast cancer, colon cancer, pancreatic cancer, lung cancer, stomach cancer, eye cancer, skin cancer and any combination thereof.

36. The method of claim 34, wherein the modified canine T cell is autologous to the subject.

37. The method of claim 34, further comprising administering an antitumor vaccine to the canine.

38. The method of claim 37, wherein the modified canine T cell and the antitumor vaccine are co-administered to the canine.

* * * * *

SEQUENCE LISTING

<160> NUMBER OF SEQ ID NOS: 7

<210> SEQ ID NO 1
<211> LENGTH: 741
<212> TYPE: DNA
<213> ORGANISM: Canis lupus familiaris

<400> SEQUENCE: 1

```
gacatcgtgc tgtcccagag ccccgccatc ctgagcgcca gccctggcga gaaagtgacc      60
atgacctgcc gggccagcag cagcctgagc ttcatgcact ggtatcagca gaagcccggc     120
agcagcccca agccctggat ctacgccacc tccaacctgg cctccggagt gcccgccaga     180
ttcagcggca gcggctccgg caccagctac agcctgacca tcagccgggt ggaggccgag     240
gacgccgcca cctactttg ccaccagtgg agcagcaacc ccctgacctt cggagccggc     300
accaagctgg aactgaagcg gggcagcacc tccggcagcg gcaagcctgg cagcggcgag     360
ggcagcacca agggccaggt gcagctgaga cagcctggcg ccgagctggt gaagccaggc     420
gccagcgtga agatgagctg caaggccagc ggctacacct taccagcta caacatgcac     480 tgggtgaaac agaccccagg acagggcctg gaatggatcg gcgccatcta ccccggcaac     540
ggcgacacct cctacaacca gaagttcaag ggcaaggcca ccctgaccgc cgacaagagc     600
agcagcaccg cctacatgca gctgtccagc ctgacctccg aggacagcgc cgtgtactac     660
tgcgccagaa gccactacgg cagcaactac gtggactact cgactactg gggccagggc     720 accacactga ccgtgtccag c                                              741
```

<210> SEQ ID NO 2
<211> LENGTH: 247
<212> TYPE: PRT
<213> ORGANISM: Canis lupus familiaris

<400> SEQUENCE: 2

```
Asp Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30
```

His Trp Tyr Gln Gln Lys Pro Gly Ser Ser Pro Lys Pro Trp Ile Tyr
          35                  40                  45

Ala Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Phe Cys His Gln Trp Ser Ser Asn Pro Leu Thr
                 85                  90                  95

Phe Gly Ala Gly Thr Lys Leu Glu Leu Lys Arg Gly Ser Thr Ser Gly
             100                 105                 110

Ser Gly Lys Pro Gly Ser Gly Glu Gly Ser Thr Lys Gly Gln Val Gln
         115                 120                 125

Leu Arg Gln Pro Gly Ala Glu Leu Val Lys Pro Gly Ala Ser Val Lys
     130                 135                 140

Met Ser Cys Lys Ala Ser Gly Tyr Thr Phe Thr Ser Tyr Asn Met His
145                 150                 155                 160

Trp Val Lys Gln Thr Pro Gly Gln Gly Leu Glu Trp Ile Gly Ala Ile
                 165                 170                 175

Tyr Pro Gly Asn Gly Asp Thr Ser Tyr Asn Gln Lys Phe Lys Gly Lys
             180                 185                 190

Ala Thr Leu Thr Ala Asp Lys Ser Ser Ser Thr Ala Tyr Met Gln Leu
         195                 200                 205

Ser Ser Leu Thr Ser Glu Asp Ser Ala Val Tyr Tyr Cys Ala Arg Ser
     210                 215                 220

His Tyr Gly Ser Asn Tyr Val Asp Tyr Phe Asp Tyr Trp Gly Gln Gly
225                 230                 235                 240

Thr Thr Leu Thr Val Ser Ser
             245

<210> SEQ ID NO 3
<211> LENGTH: 1368
<212> TYPE: DNA
<213> ORGANISM: Canis lupus familiaris

<400> SEQUENCE: 3

```
atggcctctc gggtgaccgc cctgctcctg ccgctggccc tgctgctccg tgccgcggcg      60
gctagcgaca tcgtgctgtc ccagagcccc gccatcctga cgccagccc tggcgagaaa     120 gtgaccatga cctgccgggc cagcagcagc ctgagcttca tgcactggta tcagcagaag     180
cccggcagca gcccaagcc ctggatctac gccacctcca acctggcctc cggagtgccc     240
gccagattca gcggcagcgg ctccggcacc agctacagcc tgaccatcag ccgggtggag     300
gccgaggacg ccgccaccta cttttgccac cagtggagca gcaacccct gaccttcgga     360 gccggcacca agctggaact gaagcggggc agcacctccg gcagcggcaa gcctggcagc     420
ggcgagggca gcaccaaggg ccaggtgcag ctgagacagc ctggcgccga gctggtgaag     480
ccaggcgcca gcgtgaagat gagctgcaag gccagcggct acacctttac cagctacaac     540
atgcactggg tgaaacagac cccaggacag ggcctggaat ggatcggcgc catctacccc     600
ggcaacggcg acacctccta caaccagaag ttcaagggca aggccaccct gaccgccgac     660
aagagcagca gcaccgccta catgcagctg tccagcctga cctccgagga cagcgccgtg     720
tactactgcg ccagaagcca ctacggcagc aactacgtgg actacttcga ctactggggc     780
cagggcacca cactgaccgt gtccagcgct agccccacta cgcctgcgcc gcggccaccc     840
acgcggggcg ccaccaacgc gtccaagccg gtgtctccgc gcggggagac ctgccggcct      900
```

| gcggcgggca gcgcagtgaa acaagtggg ttagacttcg cctgtgaaat ctacatctgg | 960 |
| gcacccctgg ctgggacctg cgccgtcctt ctcctgtcac tggtcatcac catcatctgc | 1020 |
| ctgagagcaa agttcggcag gagcgcggcc gcccccgagc accagcaggg ccccaaccag | 1080 |
| ctctacaacg agctcaatct gcgaggaaga gaggagtacg aggttttgga taagagacgc | 1140 |
| ggcctggacc cggagatggg aggaaagcag aggaagagga accctcagga ggtcgtgtac | 1200 |
| aatgcactgc agaaagacaa gatggcgag gcctacagtg agattgggat aaaaagcgag | 1260 |
| aaccagcgtc ggagagggaa ggggcatgat ggcctttacc aggggctcag cacggccacc | 1320 |
| aaggacacct atgatgccct ccacatgcag gccctgcccc ctcgctga | 1368 |

<210> SEQ ID NO 4
<211> LENGTH: 1500
<212> TYPE: DNA
<213> ORGANISM: Canis lupus familiaris

<400> SEQUENCE: 4

| atggcctctc gggtgaccgc cctgctcctg ccgctggccc tgctgctccg tgccgcggcg | 60 |
| gctagcgaca tcgtgctgtc ccagagcccc gccatcctga gcgccagccc tggcgagaaa | 120 |
| gtgaccatga cctgccgggc cagcagcagc ctgagcttca tgcactggta tcagcagaag | 180 |
| cccggcagca gccccaagcc ctggatctac gccacctcca acctggcctc cggagtgccc | 240 |
| gccagattca gcgcagcgg ctccggcacc agctacagcc tgaccatcag ccgggtggag | 300 |
| gccgaggacg ccgccaccta cttttgccac cagtggagca gcaacccct gaccttcgga | 360 |
| gccggcacca agctggaact gaagcggggc agcacctccg gcagcggcaa gcctggcagc | 420 |
| ggcgagggca gcaccaaggg ccaggtgcag ctgagacagc ctggcgccga gctggtgaag | 480 |
| ccaggcgcca gcgtgaagat gagctgcaag gccagcggct acaccttac cagctacaac | 540 |
| atgcactggg tgaaacagac cccaggacag ggcctggaat ggatcggcgc catctacccc | 600 |
| ggcaacggca cacctcctta caaccagaag ttcaagggca aggccaccct gaccgccgac | 660 |
| aagagcagca gcaccgccta catgcagctg tccagcctga cctccgagga cagcgccgtg | 720 |
| tactactgcg ccagaagcca ctacggcagc aactacgtgg actacttcga ctactggggc | 780 |
| cagggcacca cactgaccgt gtccagcgct agccccacta cgcctgcgcc gcggccaccc | 840 |
| acgcgggcgc ccaccaacgc gtccaagccg gtgtctccgc gcggggagac ctgccggcct | 900 |
| gcggcgggca gcgcagtgaa acaagtgggg ttagacttcg cctgtgaatt tgggcactg | 960 |
| gtggtggttg gtgcagtcct agttttctat agcttgctag taacagtggc tctttgtgcc | 1020 |
| tactggataa agagtaagag tagcaggatc cttcagagtg actacatgaa catgaccccc | 1080 |
| cggaggccgg ggcccacccg aaggcactac aacccatg ccccagcacg cgactttgca | 1140 |
| gcataccgct ccctgagagc aaagttcggc aggagcgcgg ccgcccccga gcaccagcag | 1200 |
| ggtcccaacc agctctacaa cgagctcaat ctgcgaggaa gagaggagta cgaggttttg | 1260 |
| gataagagac gcggcctgga cccggagatg ggaggaaagc agaggaagag gaaccctcag | 1320 |
| gaggtcgtgt acaatgcact gcagaaagac aagatggcag aggcctacag tgagattggg | 1380 |
| ataaaaagcg agaaccagcg tcggagaggg aaggggcatg atggccttta ccaggggctc | 1440 |
| agcacggcca ccaaggacac ctatgatgcc ctccacatgc aggccctgcc cctcgctga | 1500 |

<210> SEQ ID NO 5
<211> LENGTH: 1488
<212> TYPE: DNA
<213> ORGANISM: Canis lupus familiaris

<400> SEQUENCE: 5

```
atggcctctc gggtgaccgc cctgctcctg ccgctggccc tgctgctccg tgccgcggcg      60
gctagcgaca tcgtgctgtc ccagagcccc gccatcctga gcgccagccc tggcgagaaa     120
gtgaccatga cctgccgggc cagcagcagc ctgagcttca tgcactggta tcagcagaag     180
cccggcagca gccccaagcc ctggatctac gccacctcca acctggcctc cggagtgccc     240
gccagattca gcggcagcgg ctccggcacc agctacagcc tgaccatcag ccgggtggag     300
gccgaggacg ccgccaccta cttttgccac cagtggagca gcaacccccct gaccttcgga    360
gccggcacca gctggaact gaagcggggc agcacctccg gcagcggcaa gcctggcagc      420
ggcgagggca gcaccaaggg ccaggtgcag ctgagacagc ctggcgccga gctggtgaag     480
ccaggcgcca gcgtgaagat gagctgcaag gccagcggct acacctttac cagctacaac     540
atgcactggg tgaaacagac cccaggacag ggcctggaat ggatcggcgc catctacccc     600
ggcaacggcg acacctccta caaccagaag ttcaagggca aggccaccct gaccgccgac     660
aagagcagca gcaccgccta catgcagctg tccagcctga cctccgagga cagcgccgtg     720
tactactgcg ccagaagcca ctacggcagc aactacgtgg actacttcga ctactggggc    780
cagggcacca cactgaccgt gtccagcgct agccccacta cgcctgcgcc gcggccaccc     840
acgcgggcgc ccaccaacgc gtccaagccg gtgtctccgc gcggggagac ctgccggcct     900
gcggcgggca gcgcagtgaa acaagtgggt tagacttcg cctgtgaaat ctacatctgg      960
gcaccctgg ctgggacctg cgccgtcctt ctcctgtcac tggtcatcac catcatctgc    1020
catggcagaa agaaactcct gtatttattc aaacaaccat ttatgagacc agtacaaact   1080
gcccaagagg aagatgcctg tagttgccga tttccagaag aagaagaagg agaatgtgac   1140
ctgagagcaa agttcggcag gagcgcggcc gcccccgagc accagcaggg ccccaaccag   1200
ctctacaacg agctcaatct gcgaggaaga gaggagtacg aggttttgga taagagacgc   1260
ggcctggacc cggagatggg aggaaagcag aggaagagga accctcagga ggtcgtgtac   1320
aatgcactgc agaaagacaa gatggcagag gcctacagtg agattgggat aaaaagcgag   1380
aaccagcgtc ggagagggaa ggggcatgat ggcctttacc aggggctcag cacggccacc   1440
aaggacaccct atgatgccct ccacatgcag gccctgcccc ctcgctga              1488
```

<210> SEQ ID NO 6
<211> LENGTH: 1488
<212> TYPE: DNA
<213> ORGANISM: Canis lupus familiaris

<400> SEQUENCE: 6

```
atggcctcca gagtgaccgc cctgctgctg cccctggccc tgctgctgag ggctgctgcc      60
gctagcgaca tcgtgctgag ccagtccccct gctatcctga gcgcctcccc tggagagaag    120
gtgaccatga cctgcagggc cagctccagc ctgtccttca tgcactggta ccagcagaag     180
cctggatcca gccctaagcc ttggatctac gccaccagca acctggcctc cggagtgcct     240
gctagattca gcggatccgg aagcggcacc tcctacagcc tgaccatcag cagggtggag     300
gctgaggacg ctgctaccta cttctgccac cagtggtcca gcaatcctct gaccttcggc    360
gctggaacca agctggagct gaagaggggc tccaccagcg gatccggcaa gcctggaagc    420
ggagagggct ccaccaaggg acaggtgcag ctgaggcagc ctggagccga gctggtgaag    480
cctggcgcca gcgtgaagat gtcctgcaag gccagcggct acacctttac ctcctacaac    540
atgcactggg tgaagcagac ccctggacag ggcctggagt ggatcggagc catctaccct    600
```

```
ggcaacggcg acaccagcta caatcagaag ttcaagggca aggccaccct gaccgccgat      660
aagtccagct ccaccgccta catgcagctg agctccctga ccagcgagga ctccgccgtg      720
tactactgcg ccagatccca ctacggcagc aactacgtgg actacttcga ttactggggc      780
cagggaacca ccctgaccgt gagctccgct agccccacca cccctgctcc taggcctcct      840
accagggctc ctaccaatgc ctccaagccc gtgagcccta gaggagagac ctgcaggccc      900
gctgctggat ccgccgtgaa gaccagcggc ctggatttcg cctgcgagat ctacatctgg      960
gctcccctgg ccggaacctg cgccgtgctg ctgctgagcc tggtcatcac catcatctgc     1020
cacgccggag agaagctgct gtacctgttc aagcagccct tcatgaggcc tgtgcagacc     1080
gctcaggagg aggacgcttg ctcctgcagg ttccctgagg aggaggaggg agagtgcgat     1140
ctgagggcca agttcggccg cagcgccgct gctcctgagc accagcaggg ccctaaccag     1200
ctgtacaacg agctgaatct gaggggaagg gaggagtacg aggtgctgga caagaggagg     1260
ggcctggatc ctgagatggg aggcaagcag agaaagagga accctcagga ggtggtgtac     1320
aatgccctgc agaaggacaa gatggccgag gcctactccg agatcggcat gaagagcgag     1380
aatcagcgca aaggggcaa gggccacgat ggactgtacc agggactgtc caccgctacc     1440
aaggacacct acgatgctct gcacatgcag gccctgcctc ctaggtga                 1488

<210> SEQ ID NO 7
<211> LENGTH: 1371
<212> TYPE: DNA
<213> ORGANISM: Artificial Sequence
<220> FEATURE:
<223> OTHER INFORMATION: Artificially generated construct

<400> SEQUENCE: 7
atggccttac cagtgaccgc cttgctcctg ccgctggcct tgctgctcca cgccgccagg       60
ccgggatcag ccggatccga catcgtgctg tcccagagcc ccgccatcct gagcgccagc      120
cctggcgaga aagtgaccat gacctgccgg gccagcagca gcctgagctt catgcactgg      180
tatcagcaga agcccggcag cagccccaag ccctggatct acgccacctc caacctggcc      240
tccggagtgc ccgccagatt cagcggcagc ggctccggca ccagctacag cctgaccatc      300
agccgggtgg aggccgagga cgccgccacc tactttgcc accagtggag cagcaacccc      360
ctgaccttcg gagccggcac caagctggaa ctgaagcggg gcagcaccta cggcagcggc      420
aagcctggca gcggcgaggg cagcaccaag ggccaggtgc agctgagaca gcctggcgcc      480
gagctggtga gccaggcgc cagcgtgaag atgagctgca aggccagcgg ctacaccttt      540
accagctaca acatgcactg ggtgaaacag accccaggac agggcctgga atggatcggc      600
gccatctacc ccggcaacgg cgacacctcc tacaaccaga gttcaagggg caaggccacc      660
ctgaccgccg acaagagcag cagcaccgcc tacatgcagc tgtccagcct gacctccgag      720
gacagcgccg tgtactactg cgccagaagc cactacggca gcaactacgt ggactacttc      780
gactactggg gccagggcac cacactgacc gtgtccagcg ctagcaccac gacgccagcg      840
ccgcgaccac caacaccggc gcccaccatc gcgtcgcagc cctgtccct gcgcccagag      900 gcgtgccggc cagcggcggg gggcgcagtg cacacgaggg gctggacttt cgcctgtgat      960
atctacatct gggcgccctt ggcgggact tgtggggtcc ttctcctgtc actggttatc     1020
accctttact gcagagtgaa gttcagcagg agcgcagacg cccccgcgta ccagcagggc     1080
cagaaccagc tctataacga gctcaatcta ggacagaaga ggagtacga tgttttggac     1140 aagagacgtg gccgggaccc tgagatgggg ggaaagccga aaggaagaa ccctcaggaa     1200
```

| | | | | |
|---|---|---|---|---|
| ggcctgtaca | atgaactgca | gaaagataag | atggcggagg | cctacagtga gattgggatg | 1260 |
| aaaggcgagc | gccggagggg | caaggggcac | gatggccttt | accagggtct cagtacagcc | 1320 |
| accaaggaca | cctacgacgc | ccttcacatg | caggccctgc | ccctcgcta a | 1371 |